(12) United States Patent
Mager et al.

(10) Patent No.: US 9,494,524 B2
(45) Date of Patent: Nov. 15, 2016

(54) ASSAY FOR ANALYTES BASED ON AGGREGATION

(76) Inventors: Morgan Mager, Lorton, VA (US); Erik Daniel Aili, Linköping (SE); Molly Morag Stevens, London (GB)

(*) Notice: Subject to any disclaimer, the term of this patent is extended or adjusted under 35 U.S.C. 154(b) by 770 days.

(21) Appl. No.: 13/634,627

(22) PCT Filed: Mar. 15, 2011

(86) PCT No.: PCT/EP2011/053851
§ 371 (c)(1),
(2), (4) Date: Apr. 22, 2013

(87) PCT Pub. No.: WO2011/113813
PCT Pub. Date: Sep. 22, 2011

(65) Prior Publication Data
US 2013/0203073 A1    Aug. 8, 2013

(30) Foreign Application Priority Data
Mar. 15, 2010  (GB) .................................. 1004306.5

(51) Int. Cl.
*G01N 33/543*  (2006.01)
*G01N 21/75*   (2006.01)
*B82Y 15/00*   (2011.01)
*C12Q 1/34*    (2006.01)
*G01N 33/58*   (2006.01)

(52) U.S. Cl.
CPC ............... *G01N 21/75* (2013.01); *B82Y 15/00* (2013.01); *C12Q 1/34* (2013.01); *G01N 33/543* (2013.01); *G01N 33/5432* (2013.01); *G01N 33/588* (2013.01)

(58) Field of Classification Search
CPC ...................... B82Y 15/00; C12Q 1/34; G01N 33/542; G01N 33/5432; G01N 33/588; G01N 21/75
USPC ........................................... 436/526
See application file for complete search history.

(56) References Cited

U.S. PATENT DOCUMENTS

2006/0039962 A1* 2/2006 Heldman et al. ............. 424/450
2009/0181097 A1* 7/2009 Stevens et al. ............... 424/489

OTHER PUBLICATIONS

International Search Report and Written Opinion for PCT/EP2011/053851 mailed Oct. 5, 2011.
International Preliminary Report on Patentability for PCT/EP2011/053851 mailed Sep. 27, 2012.
Abe et al., Group II phospholipase A2 is increased in peritoneal and pleural effusions in patients with various types of cancer. Int J Cancer. Jun. 20, 1997;74(3):246-50.
(Continued)

*Primary Examiner* — Mark Shibuya
*Assistant Examiner* — Pensee Do
(74) *Attorney, Agent, or Firm* — Wolf, Greenfield & Sacks, P.C.

(57) ABSTRACT

The present invention relates to compositions, assay devices, kits and methods for detecting the presence, amount and/or activity of an analyte in a sample. In particular, the present invention relates to the detection of enzymes. The present invention also relates to methods of diagnosing diseases associated with dysregulation of enzymes, screening for modulators of enzymatic activity, candidate antimicrobial peptides and toxins.

29 Claims, 15 Drawing Sheets

(56) References Cited

OTHER PUBLICATIONS

Agarwal et al., Assessment of severity in acute pancreatitis. Am J Gastroenterol. 1991;86(10):1385-91.

Aili et al., Assembly of polypeptide-functionalized gold nanoparticles through a heteroassociation-and folding-dependent bridging. Nano Lett. Aug. 2008;8(8):2473-8. Epub Jun. 26, 2008.

Aili et al., Hybrid nanoparticle-liposome detection of phospholipase activity. Nano Lett. Apr. 13, 2011;11(4):1401-5.

Aili et al., Self-assembly of fibers and nanorings from disulfide-linked helix-loop-helix polypeptides. Angew Chem Int Ed Engl. 2008;47(30):5554-6.

Burack et al., Changes in vesicle morphology induced by lateral phase separation modulate phospholipase A2 activity. Biochemistry. Aug. 26, 1997;36(34):10551-7.

Chemburu et al., Conjugated polyelectrolyte supported bead based assays for phospholipase A2 activity. J Phys Chem B. Nov. 20, 2008;112(46):14492-9. Epub Sep. 20, 2008.

Choi et al., Sensing phosphatase activity by using gold nanoparticles. Angew Chem Int Ed Engl. 2007;46(5):707-9.

Dimitrova et al., Interaction of albumins from different species with phospholipid liposomes. Multiple binding sites system. Int J Biol Macromol. Jun. 13, 200;27(3):187-94.

Fugman et al., Lipoprotein lipase- and phospholipase A2-catalyzed hydrolysis of phospholipid vesicles with an encapsulated fluorescent dye. Effects of apolipoproteins. Biochim Biophys Acta. Sep. 12, 1984;795(2):191-5.

Gelb et al., Inhibition of phospholipase A2. FASEB J. Sep. 1994;8(12):916-24.

Green et al., Circulating phospholipase A2 activity associated with sepsis and septic shock is indistinguishable from that associated with rheumatoid arthritis. Inflammation. Oct. 1991;15(5):355-67.

Jeong et al., A novel assay to probe heparin-peptide interactions using pentapeptide-stabilized gold nanoparticles. Langmuir. Aug. 19, 2008;24(16):8794-800. Epub Jul. 22, 2008.

Kim et al., Performance of an electrochemical sensor with different types of liposomal mediators for the detection of hemolytic bacteria. Sensors and Actuators B: Chemical. Nov. 24, 2006;119(1):143-9.

Kugiyama et al., Circulating levels of secretory type II phospholipase A(2) predict coronary events in patients with coronary artery disease. Circulation. Sep. 21, 1999;100(12):1280-4.

Lehtonen et al., Phospholipase A2 as a mechanosensor. Biophys J. May 1995;68(5):1888-94.

Lelkes et al., Studies on the methodology of the carboxyfluorescein assay and on the mechanism of liposome stabilization by red blood cells in vitro. Biochim Biophys Acta. Jun. 16, 1982;716(3):410-9.

Lindahl et al., Selective inhibition of group II phospholipase A2 by quercetin. Inflammation. Oct. 1993;17(5):573-82.

Liu et al., A simple and specific assay for real-time colorimetric visualization of beta-lactamase activity by using gold nanoparticles. Angew Chem Int Ed Engl. 2007;46(46):8799-803.

MacKay et al., HIV TAT peptide modifies the distribution of DNA nanolipoparticles following convection-enhanced delivery. Mol Ther. May 2008;16(5):893-900. doi:10.1038/mt.2008.36. Epub Mar. 11, 2008.

Medley et al., Gold nanoparticle-based colorimetric assay for the direct detection of cancerous cells. Anal Chem. Feb. 15, 2008;80(4):1067-72. Epub Jan. 17, 2008.

Meier, Polymer nanocapsules. Chem. Soc. Rev. 2000;29:295-303.

Nam et al., Colorimetric bio-barcode amplification assay for cytokines. Anal Chem. Nov. 1, 2005;77(21):6985-8.

Ogawa et al., Simple and rapid colorimetric detection of cofactors of aptazymes using noncrosslinking gold nanoparticle aggregation. Bioorg Med Chem Lett. Dec. 15, 2008;18(24):6517-20. Epub Oct. 14, 2008.

Okada et al., Induced Color Change of Conjugated Polymeric Vesicles by Interfacial Catalysis of Phospholipase A2. Angew. Chem. Int. Ed. 1999;38:655-9.

Olson et al., Preparation of liposomes of defined size distribution by extrusion through polycarbonate membranes. Biochim Biophys Acta. Oct. 19, 1979;557(1):9-23.

Peng et al., A fluorescence "turn-on" ensemble for acetylcholinesterase activity assay and inhibitor screening. Org Lett. Sep. 3, 2009;11(17):4014-7.

Peyratout et al., Tailor-made polyelectrolyte microcapsules: from multilayers to smart containers. Angew Chem Int Ed Engl. Jul. 19, 2004;43(29):3762-83.

Rex et al., Quantitative studies on the melittin-induced leakage mechanism of lipid vesicles. Biochemistry. Feb. 24, 1998;37(8):2336-45.

Rose et al., Fluorogenic phospholipids as head group-selective reporters of phospholipase A activity. ACS Chemical Biology. 2006;1(2):83-92.

Sarda et al., [Actions of pancreatic lipase on esters in emulsions]. Biochim Biophys Acta. Dec. 1958;30(3):513-21. French.

Stewart, Colorimetric determination of phospholipids with ammonium ferrothiocyanate. Anal Biochem. May 1, 1980;104(1):10-4.

Wang et al., Continuous colorimetric assay for acetylcholinesterase and inhibitor screening with gold nanoparticles. Langmuir. Feb. 17, 2009;25(4):2504-7.

Wilschut et al., Action of phospholipase A2 on phospholipid vesicles. Preservation of the membrane permeability barrier during asymmetric bilayer degradation. FEBS Lett. Feb. 1, 1979;98(1):181-6.

Zeineldin et al., Detection of membrane biointeractions based on fluorescence superquenching. Langmuir. Apr. 15, 2008;24(8):4125-31. doi: 10.1021/la703575r. Epub Feb. 27, 2008.

Zhao et al., Design of gold nanoparticle-based colorimetric biosensing assays. Chembiochem. Oct. 13, 2008;9(15):2363-71. Review.

Zhao et al., Paper-based bioassays using gold nanoparticle colorimetric probes. Anal Chem. Nov. 15, 2008;80(22):8431-7. doi:10.1021/ac801008q. Epub Oct. 11, 2008.

\* cited by examiner

ASSAY FOR ANALYTES BASED ON AGGREGATION

RELATED APPLICATION

This application is a national stage filing under 35 U.S.C. §371 of international application PCT/EP2011/053851, filed Mar. 15, 2011, which was published under PCT Article 21(2) in English, the disclosure of which is incorporated by reference herein in its entirety.

The present invention relates to compositions, devices, kits and methods for detecting the presence, amount or activity of an analyte in a sample. In particular, the present invention relates to the detection of enzymes. The present invention also relates to methods of diagnosing diseases associated with dysregulation of enzymes, and methods of screening for modulators of enzymatic activity, candidate antimicrobial peptides and toxins.

Assays that enable rapid, high-sensitivity monitoring of biomolecular interactions are of immense importance for point-of-care diagnostics, drug development and detection of pathogens. Of particular interest are assays that allow the detection of enzymes in a complex or mixed sample.

Enzymes are involved in a wide range of physiological processes, and their dysregulation is implicated in a huge variety of diseases and conditions. For example, phospholipases are involved in numerous physiological processes including digestion, inflammation response, membrane remodeling and intercellular signaling. One class of phospholipases that have been intensively studied in this context are the phospholipases $A_2$ ($PLA_2$), a superfamily of enzymes that degrade phospholipids by cleaving the sn-2 acyl ester bond of glycerophospholipids to produce free fatty acids and lysolipids. Dysregulation of $PLA_2$ is a feature of many pathological conditions including atherosclerosis,[1] pancreatitis,[2] acute sepsis[3] and some forms of cancer.[4] Thus, the development of reliable assays for phospholipase activity has long been desirable.

Many assays have been developed to specifically determine $PLA_2$ concentration and activity. Traditionally, $PLA_2$ activity has been measured using methods that involve the use of radioactive materials, which are hazardous, inconvenient and time-consuming. Other traditional techniques make use of pH titration, which requires bulk volumes of reaction solutions, substrates and enzymes. Another approach has been the creation of micro- or nanoparticles made of artificial lipid analogues that undergo fluorometric[8, 9] or colorometric[10] changes upon hydrolysis. For example, U.S. Pat. No. 5,464,754 (Dennis et al) describes an assay for $PLA_2$ which comprises a synthetic substrate (an analogue of a naturally occurring phospholipid) which is hydrolysed by the $PLA_2$ to produce a free thiol. This free thiol then reacts with a reagent to produce a chromophore, which can then be detected. However, the degradation of phospholipids by phospholipases is particularly sensitive to substrate presentation in surface-catalyzed reactions. Phospholipases act primarily on aggregated phospholipids organized into lipid bilayers such as the cell membrane and thus are sensitive to the nano-scale spatial arrangement of their substrate in addition to its chemistry. Phospholipase activity on free lipid monomers is extremely low as compared to the activity on bilayers, monolayers and micelles.[5] Studies have even shown that phospholipase activity is sensitive to the phase state[6] and packing density[7] within a bilayer. Known assays relying on the use of artificial lipid analogues suffer from the drawback that the enzymatic substrate can never be identical to a natural lipid bilayer.

An alternative assay technique for enzymes makes use of liposomes. Liposomes can easily be synthesized with a wide range of chemical compositions, sizes and physical properties. Like natural cell membranes, liposomes have the ability to maintain chemical gradients, with the solution in the interior of the vesicle having a different composition from that outside. Thus, liposomes can be filled with a marker which can be used to indicate the presence of a target enzyme. U.S. Pat. No. 4,888,288 (Wagner et al) describes an enzyme immunoassay comprising liposomes containing detectable markers. These liposomes are formed from phospholipid analogs which are not hydrolysed by the target phospholipase. The target phospholipase becomes bound to the liposome, and any unbound liposomes are then removed. The remaining, bound, liposomes are then ruptured to release the marker by changing conditions such as temperature and pH or by adding a detergent.

Alternatively, some enzyme assays rely on the dispersion of markers from within the interior of a liposome as a result of the enzymatic activity of the target enzyme. WO 03/069305 (Tsao et al) describes an assay for phospholipase activity comprising liposomes containing non-fluorescent phosphatidylcholine, non-fluorescent negatively charged molecules and fluorescently labeled molecules. The target phospholipase hydrolyses the surface layer of the liposomes, resulting in a change in the intensity of the fluorescence. Liposomes have also been utilized to detect $PLA_2$ via leakage of the fluorescent dye carboxyfluorescein (CF) from the vesicle interior following lipid degradation.[11, 12] CF is self-quenched at millimolar concentrations and release (and therefore dilution) of the dye consequently results in a large increase in fluorescence intensity. Unfortunately, this approach is not very robust and is inappropriate for human diagnostic applications since human serum albumin interferes with the dye used.[13] Such limitations have led to the development of liposome phospholipase assays based on the release of other species such as electroactive[14] or superquenching[15] molecules. However, since biological fluids can contain many optically-active or redox-active compounds, these methods may be susceptible to interference.

Some alternative assay techniques make use of the unique optical and chemical properties of nanoparticles (NPs). For example, U.S. Pat. No. 7,259,252 (Mirkin et al) describes an assay for detecting nucleic acids comprising nanoparticles functionalised with complementary oligonucleotides, wherein binding of the nanoparticles to the target nucleic acids produces a detectable change. Nanoparticles have also been utilized to detect enzymes. One such approach is to employ a substrate that induces aggregation or redispersion of the nanoparticles as a result of enzymatic activity. WO 2007/063300 (Stevens et al) describes the use of aggregates comprising peptide-functionalised nanoparticles linked via a linker molecule, wherein the peptide is capable of being cleaved by the target enzyme, which cleavage results in aggregate dispersion and a detectable change. Although the immobilization of an enzyme substrate on nanoparticles has proven effective in many systems, there are concerns that it may compromise the interaction with the enzyme or limit the stability of the particles. Furthermore, this functionalization is often unique to the specific particle/molecule pair used. Because of possible variations in molecular density, activity and stability, nanoparticle-based sensors must be re-evaluated and, frequently, redesigned for each new application. The traditional intimate coupling between enzymatic substrate and nanoparticle transducer can thus limit the versatility and robustness of such systems. These variations are particularly problematic when studying processes affected by the physical as well as chemical state of the biomolecules involved.

Thus, there is a need to develop an alternative assay which overcomes these many and varied limitations. The present invention provides an assay which uniquely integrates the release of linker molecules from carrier particles with controllable signal particle aggregation to provide an assay that is sensitive, robust, specific, flexible and biologically relevant.

The present invention will be described further with reference to the accompanying, non-limiting drawings, in which:

FIG. 1 is a pictographic representation of one embodiment of the present invention comprising a signal particle (1), a carrier particle (2) and a linker molecule (3). Said signal particle (1) comprises a core (4) on which are immobilised binding moieties (5). The carrier particle (2) comprises a surface layer of amphipathic molecules (6) enclosing an interior volume (7).

(A) (i) in the presence of $PLA_2$(———); (ii) in the presence of $PLA_2$ and ethylenediaminetetraacetic acid (EDTA) (·········) and (iii) in the absence of the peptide linker molecule ( - - - ); and (B) (i) in the absence of HSA (———); (ii) when addition of $PLA_2$ follows the addition of HSA (·········) and (iii) when the addition of HSA follows the addition of $PLA_2$ ( - - - ).

Figure 4:
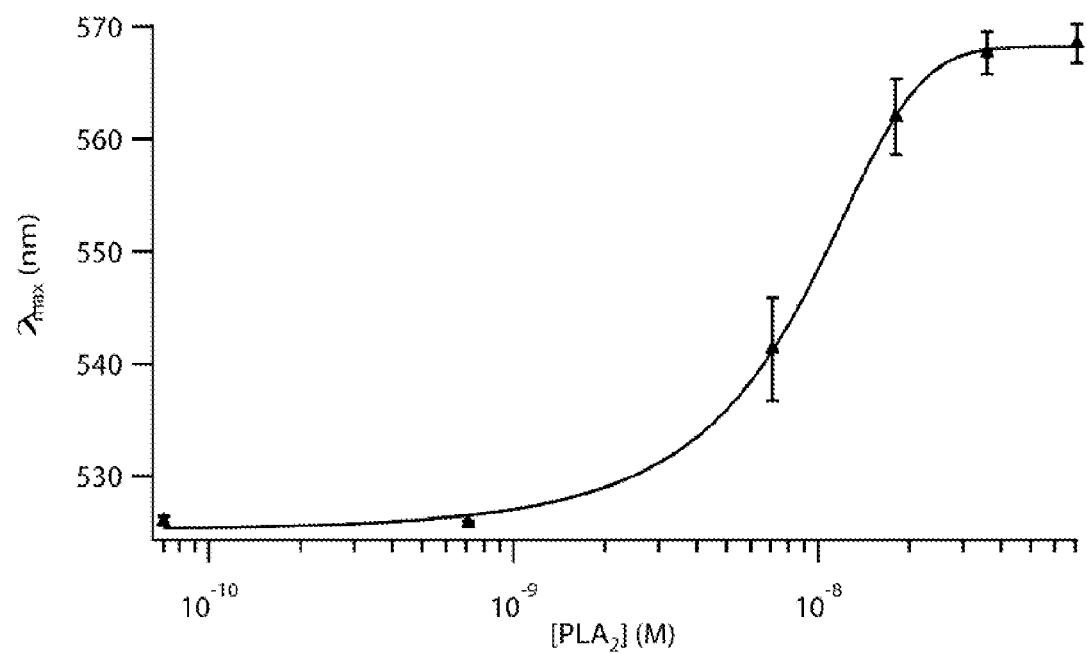

FIG. 4 is a calibration curve showing nanoparticle spectral shift magnitudes for various $PLA_2$ concentrations at room temperature after addition of HSA. The maximum shift intensity is plotted ±SEM for each point.

Figure 5:
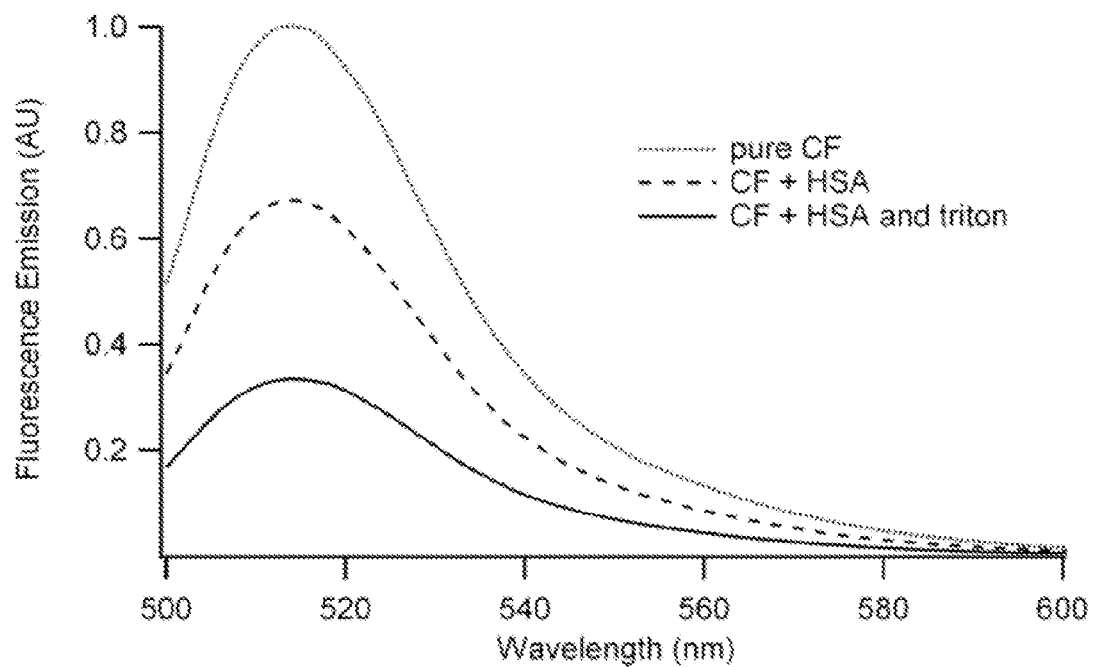

FIG. 5 is a plot of the fluorescence emission of a prior art carboxyfluorescein (CF)-based assay composition as a function of wavelength; (i) for a 0.75 µM solution of CF (·········); (ii) for a 0.75µM solution of CF after the addition of 30 µM of human serum albumin (HSA) ( - - - ); and (iii) for a 0.75 µM solution of CF after the addition of 30 µM of HSA and 0.17 mM Triton X-100 (———).

Figure 6:
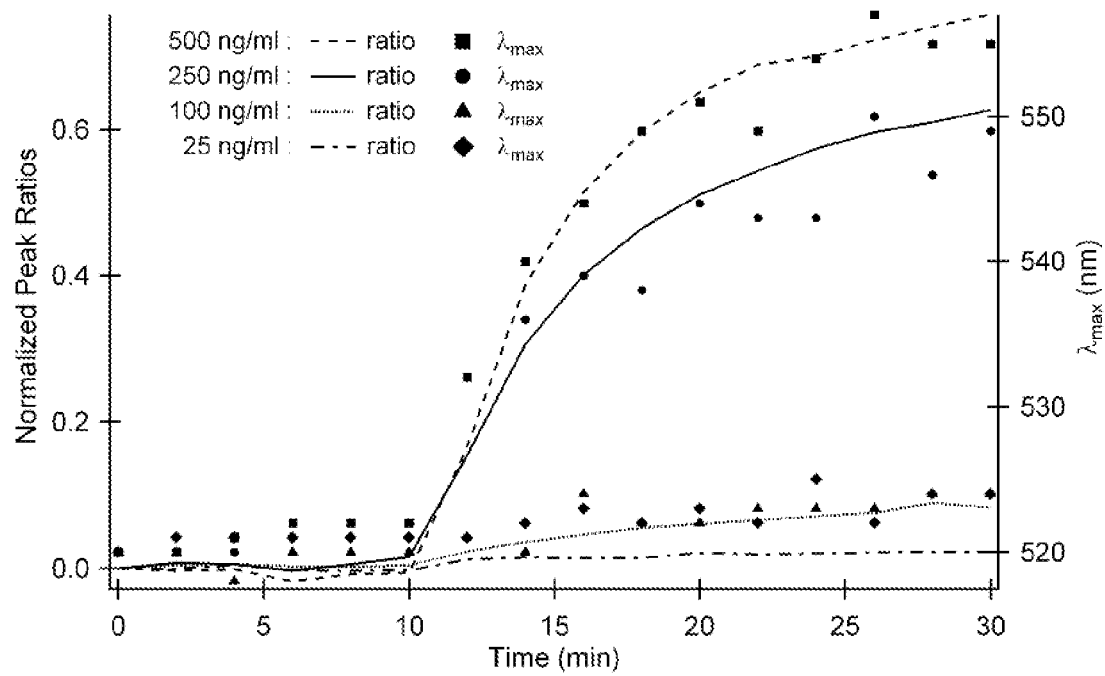

FIG. 6 is a plot of the absorption of a composition of the present invention as a function of time, expressed as (a) normalised peak ratios of absorption at 520 nm and 570 nm (lines) and (b) the wavelength of the absolute maximum of the absorption peak (points) over time, after treatment with $PLA_2$ at a concentration of (i) 500 ng/ml; (ii) 250 ng/ml; (iii) 100 ng/ml; and (iv) 25 ng/ml, at room temperature after addition of HSA.

Figure 7:
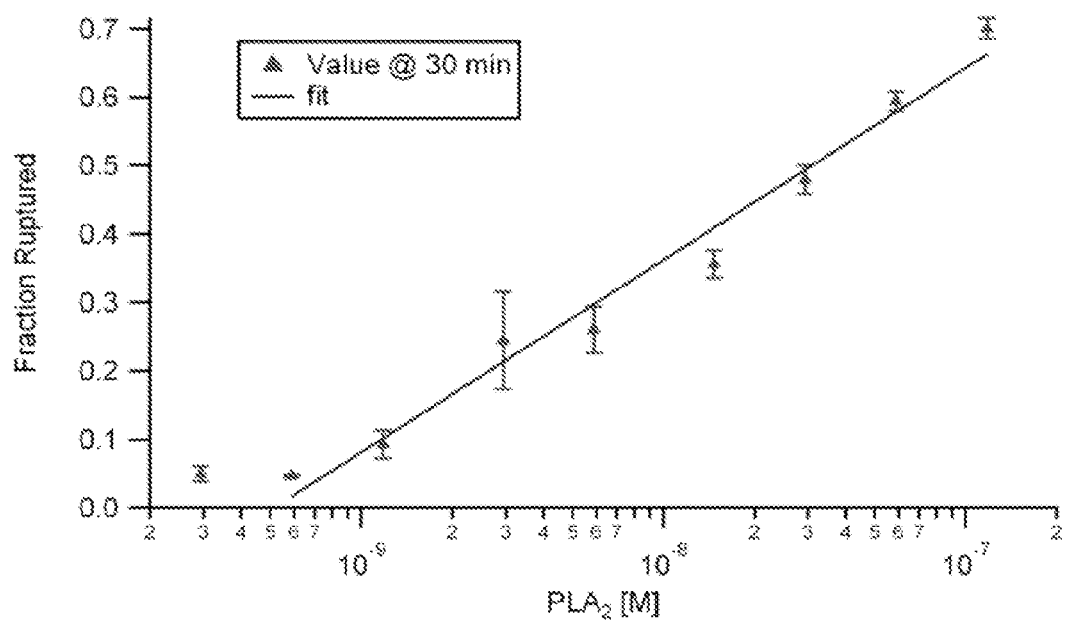

FIG. 7 is a plot of the fraction of carboxyfluorescein-filled liposomes ruptured after 30 minutes incubation with the indicated concentration of $PLA_2$. Data shown are mean±SEM.

Figure 8:
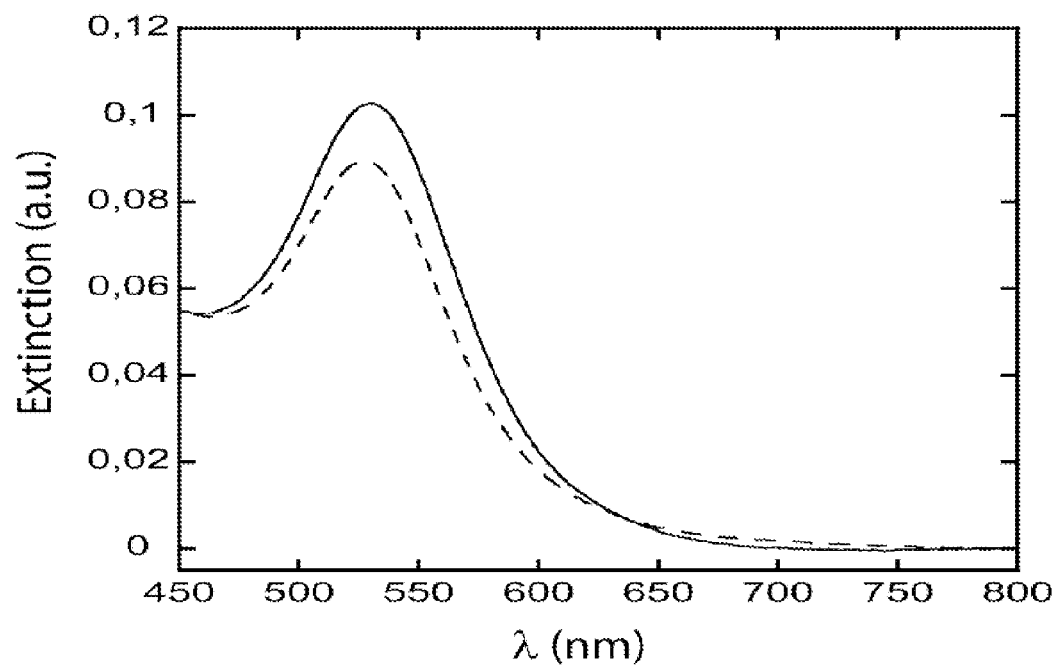

FIG. 8 is a plot of the optical extinction of a composition according to the present invention as a function of wavelength after a 12 hour incubation (i) with 70 pM of $PLA_2$ (———) and (ii) without $PLA_2$ ( - - - ) at room temperature.

Figure 9:
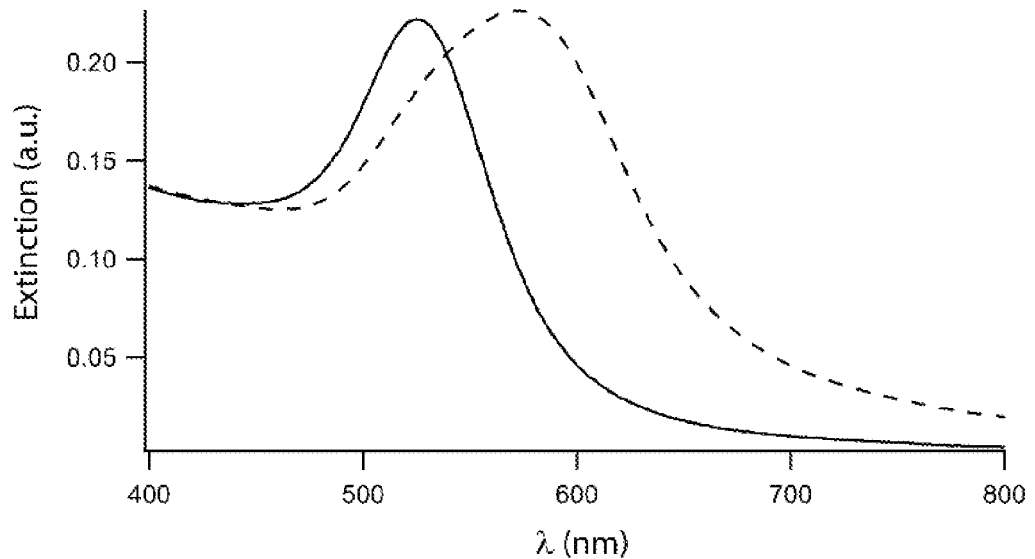

FIG. 9 is a plot of the optical extinction of a solution of liposomes containing 1.5 mol % of PEG-lipids as a function of wavelength (i) before the addition of $PLA_2$ (———) and (ii) 8 minutes after addition of 0.7 nM $PLA_2$ ( - - - ) at room temperature.

Figure 10:
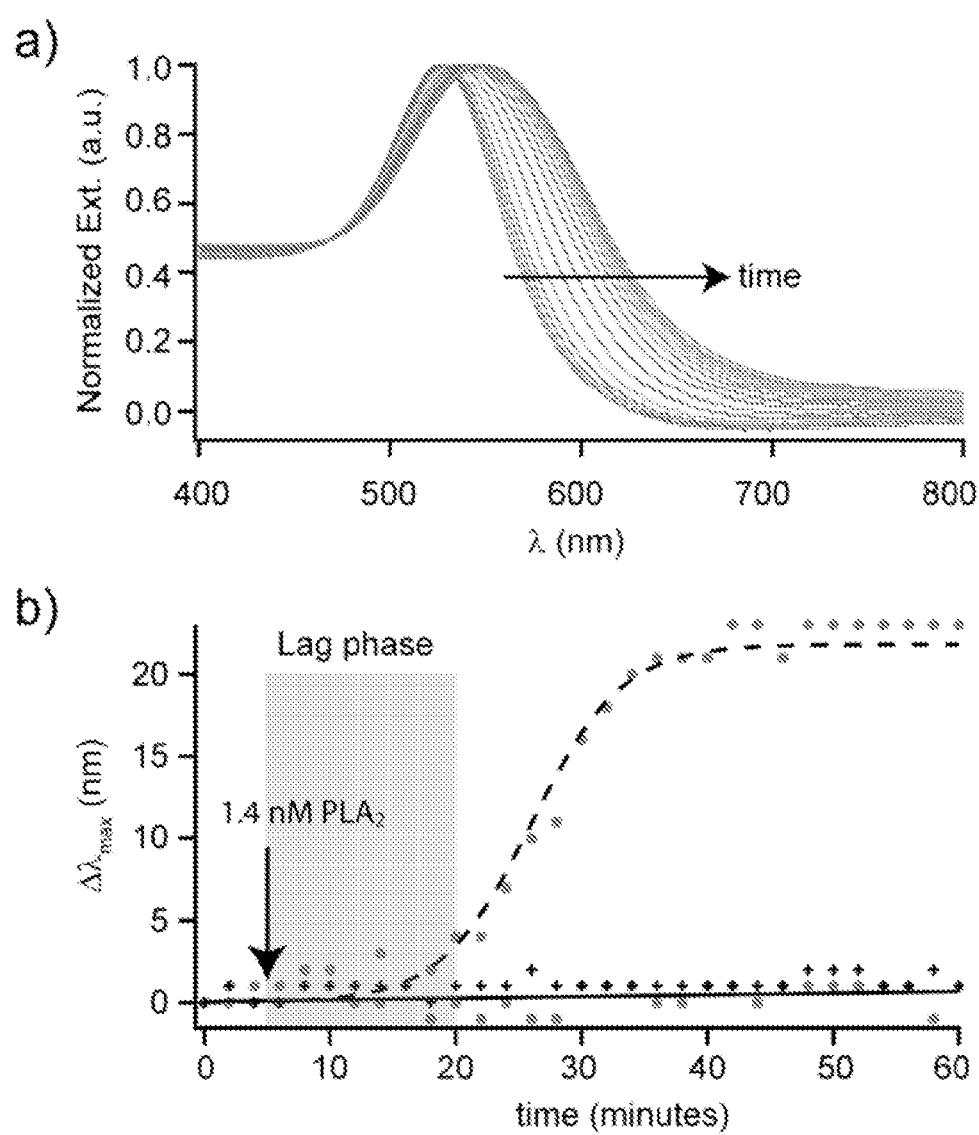

FIG. 10a) is a plot of the normalized optical extinction as a function of wavelength for a solution of $JR2KC_2$-loaded liposomes and JR2EC-modified gold nanoparticles after the addition of $PLA_2$ at 37° C.

FIG. 10b) is a plot of peak shift ($\Delta\lambda_{max}$) over time for a solution of $JR2KC_2$-loaded liposomes and JR2EC-modified gold nanoparticles after the addition of $PLA_2$, under the following conditions: i) in the presence of $Ca^{2+}$( - - - ); ii) in the absence of $Ca^{2+}$(———) and iii) using nanoparticles functionalised with a modified form of JR2EC in which L-alanines are replaced with D-alanines, rendering the peptide unable to fold and form the heterotrimeric complex (+).

Figure 11:
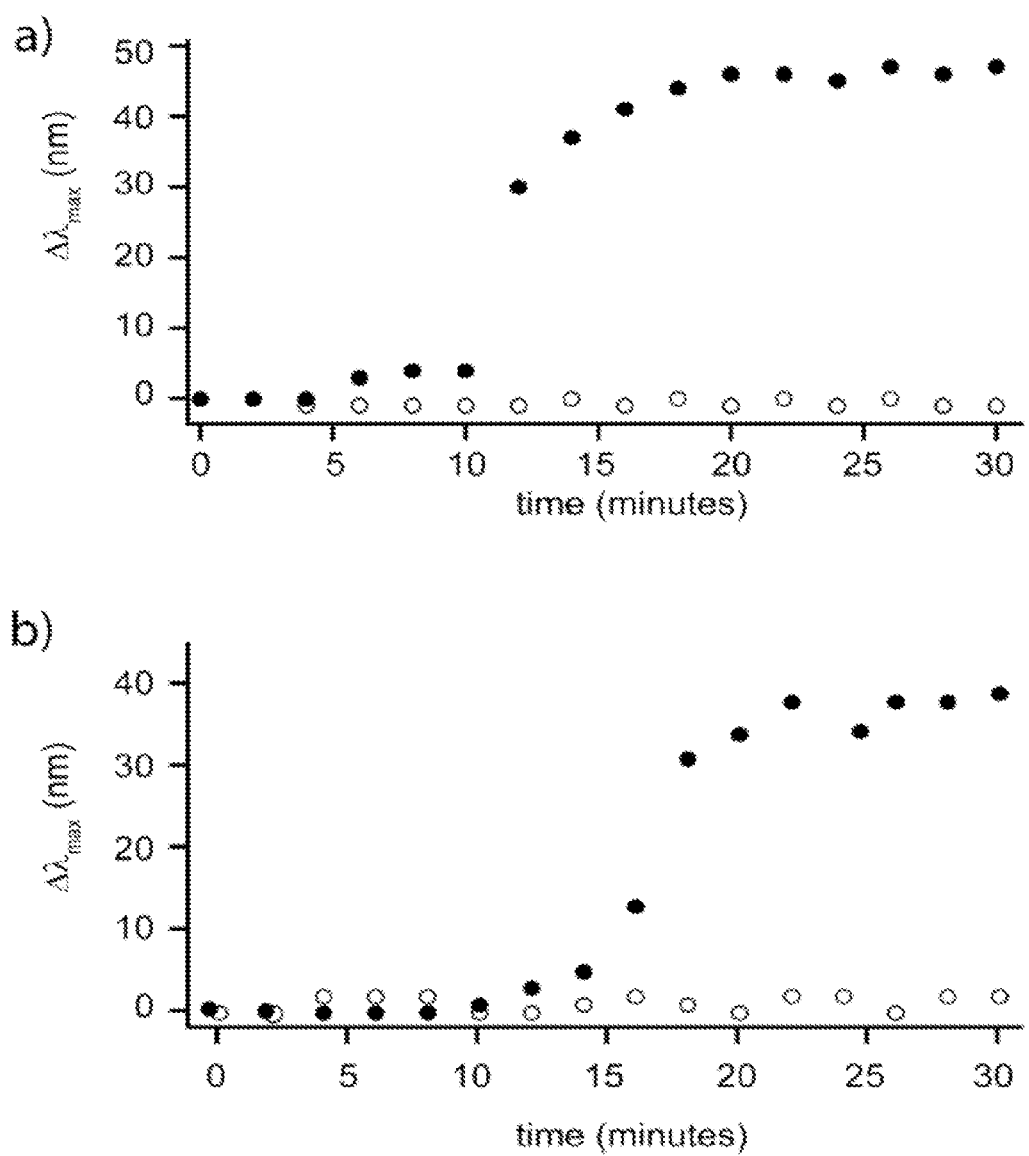

FIG. 11a) is a plot of peak shift ($\Delta\lambda_{max}$) over time for a solution of $JR2KC_2$-loaded liposomes and JR2EC-modified gold nanoparticles after storage for 15 weeks, under the following conditions: i) after addition of 7 nM $PLA_2$ (●) and ii) in the absence of $PLA_2$ (○).

FIG. 11b) is a plot of peak shift ($\Delta\lambda_{max}$) over time for a solution of PEG-grafted, $JR2KC_2$-loaded liposomes and JR2EC-modified gold nanoparticles at room temperature, under the following conditions: i) after addition of 7 nM $PLA_2$ (●) and ii) in the absence of $PLA_2$ (○).

Figure 12:
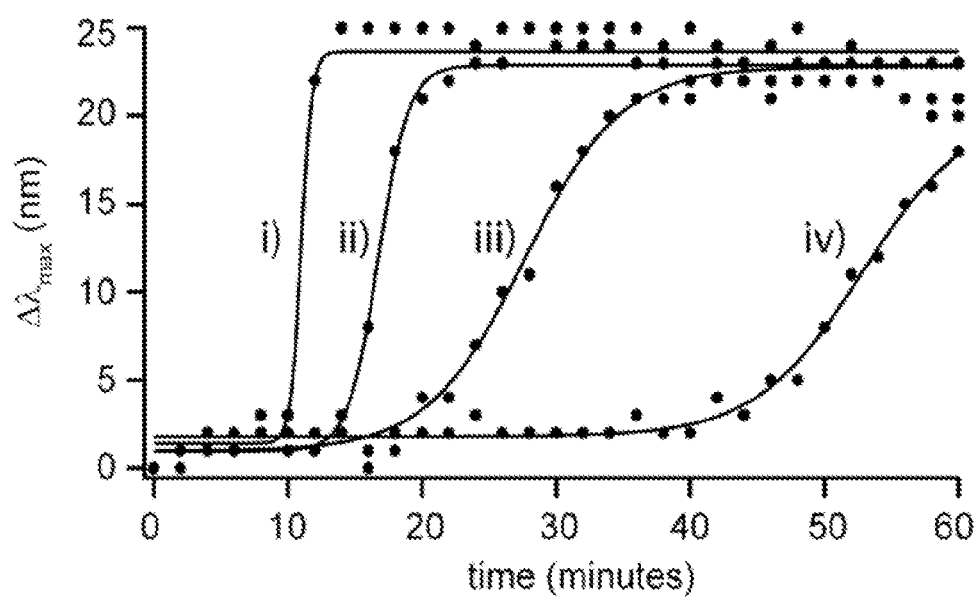
Figure 12:
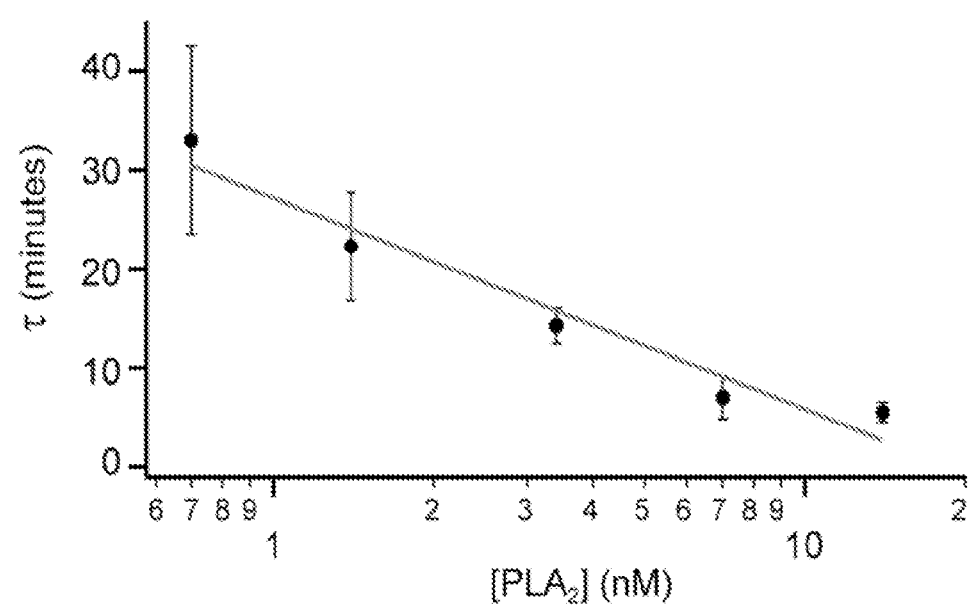

FIG. 12a) is a plot of peak shift ($\Delta\lambda_{max}$) over time for a solution of $JR2KC_2$-loaded liposomes and JR2EC-modified gold nanoparticles at 37° C. in the presence of 0.5 mM $Ca^{2+}$, following the addition at time point T=5 minutes of: i) 7 nM $PLA_2$ (line labelled i)); ii) 3.5 nM $PLA_2$ (line labelled ii)); iii) 1.4 nM $PLA_2$ (line labelled iii)); or iv) 700 pM $PLA_2$ (line labelled iv)). The lines are drawn as a guide for the eye.

FIG. 12b) shows the length of the lag time (τ) as a function of $PLA_2$ concentration ($R^2$=0.97). Error bars are standard error of the mean, n≥3.

Figure 13:
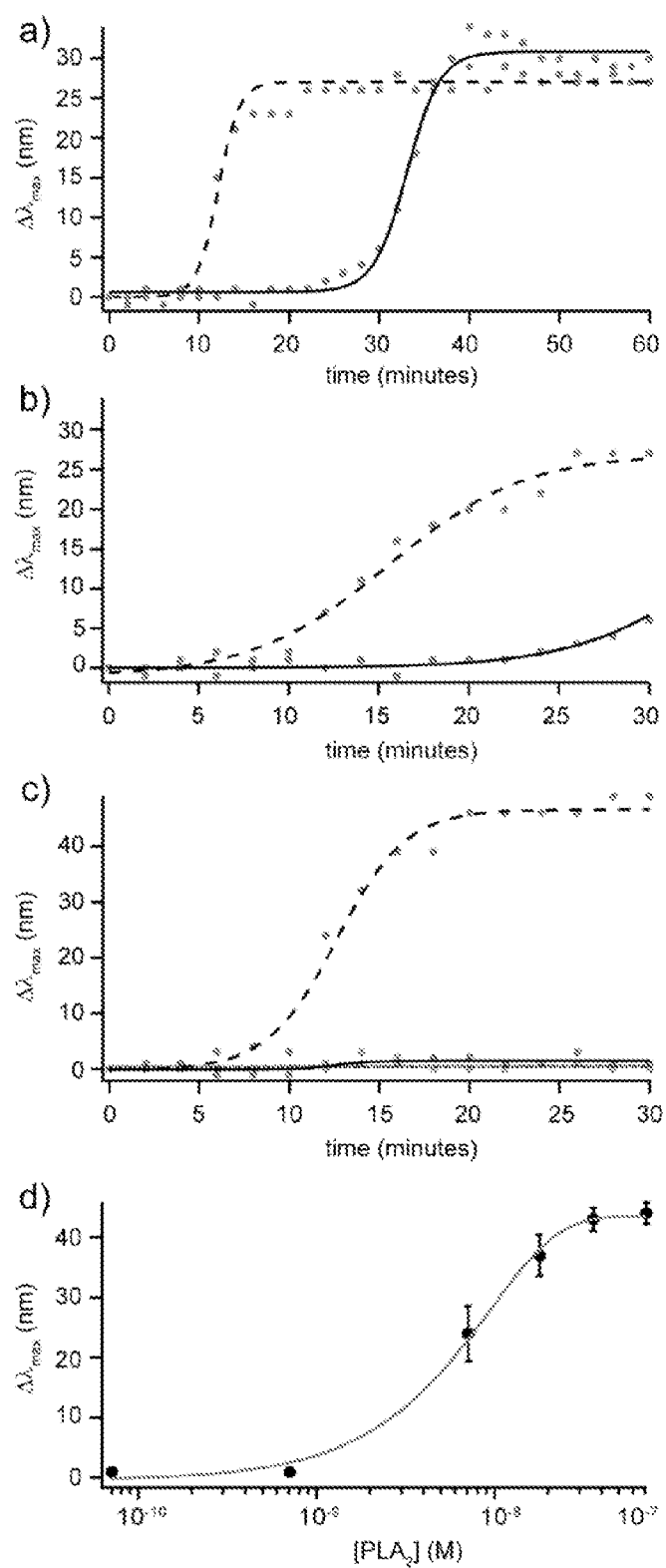

FIG. 13a) is a plot of peak shift ($\Delta\lambda_{max}$) over time for a solution of $JR2KC_2$-loaded liposomes and JR2EC-modified gold nanoparticles following addition of 7 nM $PLA_2$ under the following conditions: i) at room temperature (———) or ii) 37° C. ( - - - ).

FIG. 13b) is a plot of peak shift ($\Delta\lambda_{max}$) over time for a solution of $JR2KC_2$-loaded liposomes and JR2EC-modified gold nanoparticles following addition of 7 nM $PLA_2$ at room temperature under the following conditions: i) after the addition of 4 mg/ml HSA ( - - - ) or ii) in the absence of HSA (———).

FIG. 13c) is a plot of peak shift ($\Delta\lambda_{max}$) over time for a solution of $JR2KC_2$-loaded liposomes and JR2EC-modified gold nanoparticles at room temperature under the following conditions: i) in the presence of 4 mg/mL HSA, 70 nM $PLA_2$ and $Ca^{2+}$( - - - ); ii) in the presence of 4 mg/mL HSA and 70 nM $PLA_2$ but in the absence of $Ca^{2+}$(·········) or iii) in the presence of 4 mg/mL HSA and 70 nM $PLA_2$ but in the absence of $JR2KC_2$ (———).

FIG. 13d) is a plot of peak shift ($\Delta\lambda_{max}$) as a function of $PLA_2$ concentration for a solution of $JR2KC_2$-loaded liposomes and JR2EC-modified gold nanoparticles, 10 minutes after addition of 4 mg/ml HAS at room temperature. Error bars are standard error of the mean, n≥3. Lines drawn as a guide for the eye.

Figure 14:
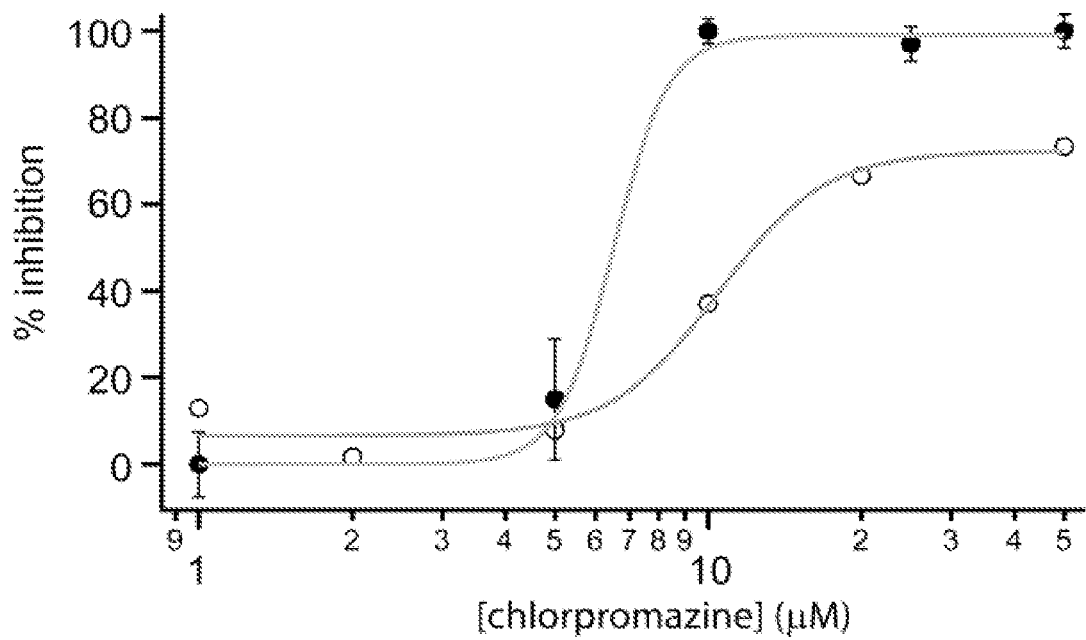

FIG. 14 is a plot of percentage inhibition of $PLA_2$ as a function of chlorpromazine concentration at 37° C., as determined using the nanoparticle-peptide assay comprising a solution of $JR2KC_2$-loaded liposomes and JR2EC-modified gold nanoparticles (●) and a traditional carboxyfluorescein (CF)-based fluorescence assay (○). Error bars are standard error of the mean, n≥3.

Figure 15:
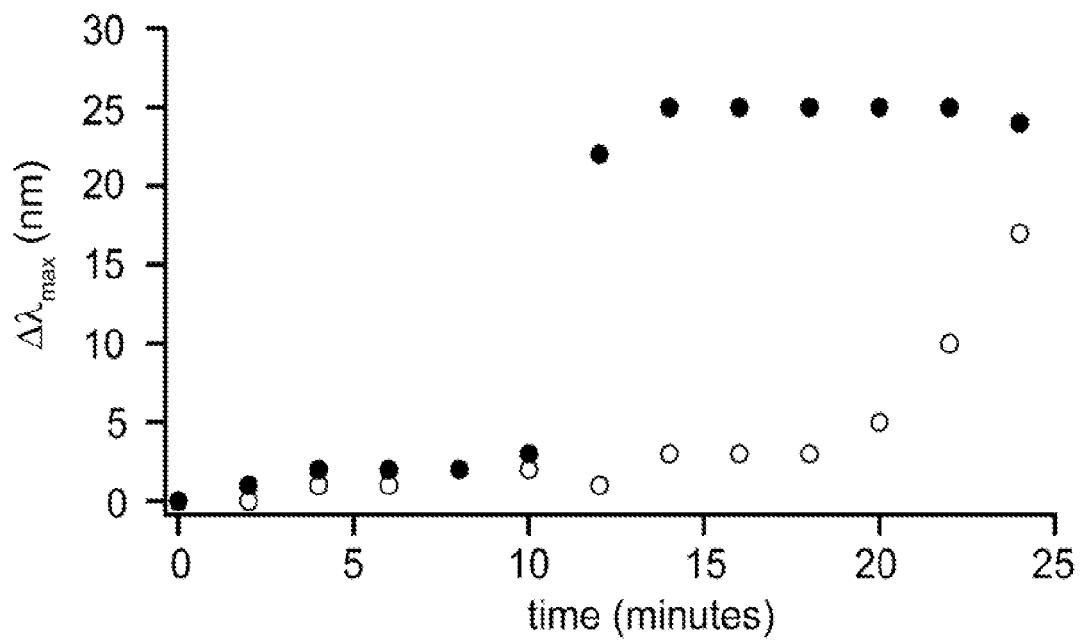

FIG. 15 is a plot of peak shift ($\Delta\lambda_{max}$) as a function of time for a solution of JR2KC$_2$-loaded liposomes and JR2EC-modified gold nanoparticles after addition of 7 nM PLA$_2$ under the following conditions: i) in the absence of chlorpromazine (●) or ii) in the presence of 10 μM chlorpromazine (○).

A first aspect of the present invention provides a composition comprising:
  a) a plurality of signal particles functionalised with at least one binding moiety;
  b) a plurality of carrier particles;
  c) a plurality of linker molecules contained within said carrier particles, wherein said linker molecules are capable of associating with the at least one binding moiety on said signal particles to cause aggregation of said signal particles.

The signal particles, also known as transducer particles, can comprise any suitable particles capable of aggregating when placed in contact with the linker molecule. An important property of the signal particles is that their aggregation results in a detectable or measurable change.

Suitable signal particles include microparticles and nanoparticles. Preferably, the particles are large enough to display significant size-dependent optical properties, but small enough to remain dispersed in solution. Preferably, the particles comprise nanoparticles with a diameter in the range 2 nm-100 nm. The nanoparticles may comprise, for example, spherical nanoparticles, nanotubes or nanorods. Suitable nanoparticles include metal nanoparticles, semiconducting nanoparticles, core-shell nanoparticles and polymer nanoparticles. Preferred metal nanoparticles include those comprising gold, silver, ferrous metals or cobalt-based metals. Suitable semiconducting nanoparticles include quantum dots. Suitable core-shell nanoparticles include those comprising a metal shell and a dielectric or semiconducting core, or a dielectric or semiconducting shell and a metal core, or a dielectric or semiconducting shell and a dielectric or semiconducting core. Suitable polymer particles include polymer microcapsules and nanocapsules[23, 24] comprising particles with a delineated core and shell. Preferably, the signal particles are gold nanoparticles.

The signal particles used can be tailored to the particular assay in question. For example, gold and silver nanoparticles are particularly suitable for those applications where the desired measurable change comprises a change in optical absorption. Nanoparticles comprising ferrous and cobalt-based metals are particularly suitable for those applications where the desired measurable change comprises a change in magnetic properties. Under some circumstances, the size of the signal particle can determine the absorption spectrum of the composition before and after aggregation. This is particularly true for gold nanoparticles and quantum dots. The size of the signal particle can be optimised to provide a spectral shift within a particular region of the electromagnetic spectrum. For example, it may be desirable to provide a signal particle of a size that produces absorption spectra within a region of the visible spectrum that is not absorbed by the sample. Under some circumstances, it is desirable to provide a signal particle of a size that produces absorption spectra within the region of the electromagnetic spectrum near to that corresponding to infra-red. Bodily tissues are readily transparent to those wavelengths, and such signal particles would therefore be particularly useful for in vivo applications.

The signal particles are functionalised with at least one binding moiety. Preferably, each signal particle is functionalised with one, two, three, four or more binding moieties.

The binding moieties may be temporarily or permanently attached to the surface of the signal particles by any suitable means. For example, the binding moieties may be covalently linked to the signal particles, adsorbed or immobilised on the surface of the signal particles, or otherwise conjugated thereto. The binding moieties are preferably complementary to the linker molecules and are capable of associating with the linker molecules to facilitate aggregation of the signal particles. The association may be a homo-association (if the binding moieties and linker molecules are the same type of molecule) or, more preferably, a hetero-association (if the binding moieties and linker molecules are different types of molecule).

The binding moiety may comprise any suitable molecule that is capable of being attached to the surface of the signal particle and of associating with the linker molecules. Suitable binding moieties include carbohydrates and polymers such as proteins, peptides, polypeptides, peptoids, peptide nucleic acids, oligonucleotides and synthetic derivatives thereof. Suitable proteins include avidin, streptavidin, neutravidin, captavidin, and antibodies. Suitable polypeptides include those that undergo a supramolecular assembly and include coiled-coil polypeptides and helix-loop-helix polypeptides, particularly those with $2^{nd}$ or higher order interactions such as dimerisation. A particularly preferred polypeptide is a polypeptide according to SEQ ID NO. 1, termed JR2EC:

```
                                      (SEQ ID NO. 1)
NAADLEKAIEALEKHLEAKGPCDAAQLEK QLEQAFEAFERAG
```

The binding moiety may also comprise a polypeptide at least 80%, at least 90%, at least 95% or at least 99% identical to SEQ ID NO. 1. Other suitable binding moieties include biotin and, wherein the linker molecules are antibodies, any antigens that bind thereto. Preferably, the binding moiety is not an oligonucleotide.

In one embodiment, two, three, four or more different types of binding moiety may be co-immobilised on the surface of the signal particles.

The signal particle may also be co-functionalised with further useful moieties. For example, the signal particle may be co-functionalised with protein-repellant molecules or spacer moieties such as polyethylene glycol (PEG) to reduce non-specific adsorption.

The carrier particle can comprise any suitable particle which is capable of containing the linker molecules and then releasing the linker molecules upon contact with a release substance. As used herein the phrase "release substance" refers to any substance capable of degrading or otherwise permeabilising the carrier particle to allow the linker molecules to escape into solution and contact the signal particles. Examples include antimicrobial peptides, toxins and enzymes. Preferably, the enzymes are lipases, including phospholipases such as PLA$_2$. As used herein, 'degradation' of the carrier particle or of the surface layer thereof is intended to refer to any change in the structure of the carrier particle which facilitates the release of the linker molecules.

The carrier particle may comprise a solid particle or a liquid core surrounded by a surface layer.

The surface layer is preferably a thin polymer membrane or a layer of amphipathic molecules. Suitable amphipathic molecules include artificially generated amphipathic molecules such as engineered block copolymers, and lipids such as phospholipids. The surface layer of the carrier particle preferably comprises a lipid mixture. In one embodiment, this lipid mixture may be an undefined mixture extracted from cells or tissues. Alternatively, the lipid mixture may be carefully defined. The lipids may be synthetic, but are preferably chemically and molecularly identical or nearly identical to natural lipids. In one embodiment, the surface layer comprises 0-35% cholesterol. Increasing amounts of cholesterol have been found to decrease the lipase degradation rate and could thus be used to tune the response of the system if less sensitivity is desired, for example to detect higher enzyme levels. In another embodiment, the surface layer comprises 0-25% lipids grafted with polymers such as polyethylene glycol (PEG). As described in Example 9, PEG grafting produces a larger redshift of the Plasmon peak without the need for HSA. In addition, as described in Example 15, PEG grafting produces a faster release of peptides and thus a reduced lag phase, and a slightly higher total response.

Preferably, the surface layer of the carrier particle is specifically degradable by an enzyme (a "release substance"). Preferably, the enzyme is a lipase, more preferably a phospholipase such as $PLA_2$. The surface layer of the carrier particle can be tailored to the particular assay in question, as the type of molecules, the phase state of the molecules and the packing density of the molecules will determine the particular enzyme for which the surface layer will be an enzymatic substrate. Thus, where the target enzyme is a lipase, the molecules may primarily comprise lipids. Where the target enzyme is a phospholipase, the lipids may primarily comprise phospholipids.

The liquid core of the carrier particle preferably comprises an oily or aqueous solution.

In those embodiments where the carrier particles comprise a liquid core surrounded by a surface layer, the linker molecules may be contained within the liquid core, or within the surface layer.

Preferably, the carrier particles are selected from the group comprising liposomes, micelles, nanocapsules, microcapsules and polymeric particles, although other suitable carrier particles will be known to one of skill in the art. Preferably, the carrier particle is a liposome.

The linker molecules may comprise any suitable molecules capable of facilitating the aggregation of the signal particles. The linker molecules must therefore be capable of associating with one or more of the binding moieties on the signal particles. As used herein, the phrase "capable of associating" means that the linker molecules will associate with the binding moieties on the signal particles under appropriate conditions, i.e. when placed in contact with the binding moieties following release from the carrier particle. Preferably, each linker molecule is capable of associating with one or more binding moieties on a first signal particle, and one or more binding moieties on a second signal particle. The association of a linker molecule with one or more binding moieties on a first signal particle, and one or more binding moieties on a second signal particle, will link the first and second signal particles. Thus, the association of multiple linker molecules with binding moieties on multiple signal particles will form an aggregation of signal particles. Preferably, each linker molecule can associate with two, three, four or more binding moieties on each signal particle.

In one embodiment, the linker molecules are also able to homo-associate or crosslink with other linker molecules. For example, under certain conditions, linker molecules such as $JR2KC_2$ may form fibres. The formation of fibres within the carrier particle may enhance the stability of the system by reducing leakage of the linker molecules from the carrier particles in the absence of the release substance.

The linker molecules may comprise a polymer. Preferably, the polymer is a protein, peptide or a polypeptide. Suitable proteins include avidin, streptavidin, neutravidin, captavidin and antibodies. Suitable polypeptides include coiled-coil and helix-loop-helix polypeptides, particularly those with $2^{nd}$ or higher order interactions such as dimerisation. A particularly preferred polypeptide is $JR2KC_2$[26], which comprises a covalently linked pair (dimer) of JR2KC polypeptides, which contain or comprise the sequence according to SEQ ID NO. 2:

```
                                        (SEQ ID NO. 2)
NAADLKKAIKALKKHLKAKGPCDAAQLKKQLKQAFKAFKRAG
```

$JR2KC_2$ can associate with two binding moieties on two separate signal particles and fold into two disulphide-linked four-helix bundles. The linker molecule may also comprise a dimer of a polypeptide containing or comprising a sequence at least 80%, at least 90%, at least 95% or at least 99% identical to SEQ ID NO. 2. Other suitable linker molecules include biotin and, where the binding moieties are antibodies, any antigens that bind thereto.

The linker molecule and binding moiety may form, for example, a biotin-avidin conjugate pair, an antibody-antigen conjugate pair or a JR2EC-$JR2KC_2$-JR2EC conjugate pair, as discussed below.

In a particularly preferred embodiment of the present invention, the signal particle is functionalised with JR2EC and the linker molecule comprises $JR2KC_2$. In this embodiment, the molecular basis of the crosslinking reaction between the binding moiety and the linker molecule is a folding-dependent hetero-association between the synthetic de novo designed polypeptides. JR2EC and JR2KC are designed to fold into helix-loop-helix motifs and heterodimerize into four-helix bundles in solution. Both peptides have a cysteine residue located in the loop region which was utilized for immobilising JR2EC on gold nanoparticles and for covalently linking two of the JR2KC-monomers via a disulphide-bridge. In solution, the oxidized form of JR2KC (termed $JR2KC_2$) associates with two of the complementary peptides (JR2EC) to form a hetero-trimeric complex that folds into two disulphide-linked four-helix bundles. When both peptides are oxidized, hetero-association induces the assembly of peptide fibers of disulphide-linked four-helix bundles.[16] Gold nanoparticles functionalized with JR2EC aggregate rapidly and extensively in the presence of nanomolar concentrations of $JR2KC_2$. The resulting red-shift of the plasmon peak varies with the concentration of the linker molecule[26].

The composition may additionally comprise molecules designed to enhance the rate of enzymatic degradation of the surface layer of the carrier particle, or molecules designed to enhance the rate of carrier particle leakage. For example, the composition may additionally comprise albumin such as human serum albumin (HSA) or bovine serum albumin (BSA). As described in Example 4 and Example 13, HSA can be used to enable better and faster disassembly of the carrier molecule.

The composition may also comprise one or more preservatives that aid in the preservation of the components. In particular, the composition may comprise preservatives which protect components such as liposomes in the event of drying or freeze-drying. Suitable preservatives include sugars such as trehalose, which stabilize lipid bilayers and proteins during dehydration and rehydration.

The composition may comprise a dispersed solution of the above-identified components. Preferably, the dispersed solution comprises an aqueous solution.

The composition, or a solution thereof, preferably comprises a pH in the range 6-8. More preferably, the pH lies in the range 7-8. Most preferably, the pH lies in the range 7.2-7.6, and is preferably approximately 7.4.

In a preferred embodiment, the composition comprises a plurality of nanoparticles, a plurality of liposomes and a plurality of linker molecules encapsulated within the liposomes. In a particularly preferred embodiment, the composition comprises a plurality of gold nanoparticles functionalised with JR2EC polypeptides, a plurality of liposomes, and a plurality of JR2KC$_2$ polypeptides encapsulated within the liposomes.

The composition according to the first aspect of the present invention is very stable in storage. As described in Example 3 and in Example 10, a composition comprising liposomes encapsulating JR2KC$_2$ shows remarkable stability in storage in comparison with CF-loaded liposomes. After 15 weeks of storage at 4° C. there was no detectable background leakage, but the liposomes maintained full responsiveness towards PLA$_2$.

The composition according to the first aspect of the present invention is also relatively inexpensive, as the materials utilized are relatively inexpensive in themselves, and only a small amount of each component is required to provide sufficient composition to test a sample for an analyte.

A second aspect of the present invention provides a carrier particle as described in relation to the first aspect of the present invention. Preferably, the carrier particle comprises a liquid core surrounded by a surface layer, and contains JR2KC$_2$ or a dimer of polypeptides having a sequence at least 80%, at least 90%, at least 95% or at least 99% identical to SEQ ID NO. 2:

```
                                              (SEQ ID NO. 2)
NAADLKKAIKALKKHLKAKGPCDAAQLKKQLKQAFKAFKRAG
```

Preferably, said surface layer comprise amphipathic molecules. Preferably, said carrier particle is a liposome.

A third aspect of the present invention provides the use of the composition according to the first aspect of the present invention or the carrier particles according to the second aspect of the present invention. As described above, when a composition of the present invention is in the presence of a release substance such as an enzyme, an antimicrobial peptide or a toxin, the release of the linker molecules from the carrier particles results in a detectable aggregation of the signal particles. The composition of the first aspect of the present invention therefore has a number of uses, including detecting analytes such as enzymes, screening for modulators of enzymatic activity and screening for candidate antimicrobial particles and toxins. These uses are discussed in more detail below.

A fourth aspect of the present invention provides an assay device for detection of an analyte in a sample, wherein the assay device comprises a composition according to the first aspect of the present invention.

As used herein, the phrase 'for the detection of an analyte in a sample' includes the detection of the presence of an analyte in a sample, the measurement of the amount or concentration of an analyte in a sample, the detection of analyte activity in a sample, and the measurement of the amount of analyte activity in a sample. Preferably, the analyte is an enzyme. Preferably the enzyme is a lipase, more preferably a phospholipase, most preferably PLA$_2$.

The composition according to the first aspect of the present invention, or one or more components thereof, may be provided as an aqueous solution. Alternatively, the composition, or one or more of the components thereof, could be freeze-dried for storage and subsequently rehydrated before use.

In one embodiment, the assay device comprises a dip-stick coated with the composition according to the first aspect of the present invention. In an alternative embodiment, the assay device comprises a lateral flow device comprising the composition according to the first aspect of the present invention. Preferably, the composition is dried or freeze-dried onto a surface of the dip-stick or lateral flow device. Exposure of the stick or the lateral flow device to a fluid sample will dissolve the components and return them to solution.

A fifth aspect of the present invention provides a kit for detection of an analyte in a sample, comprising a composition according to the first aspect of the present invention, or the individual components thereof.

Preferably, the analyte is an enzyme. Preferably, said enzyme is a lipase, preferably a phospholipase such as PLA$_2$.

The kit may further comprise one or more compartments containing the composition according to the first aspect of the present invention, or one or more of the individual components thereof. Preferably, each component is contained within a separate compartment. Each component may be stored as a solution, or in freeze-dried form. Immediately prior to use, solutions of the various components can be mixed together in the appropriate quantities to provide the composition according to the first aspect.

A sixth aspect of the present invention provides a method for detection of an analyte in a sample comprising the steps of:
i) contacting said sample with the composition according to the first aspect of the present invention, wherein said analyte degrades said carrier particle, releasing said linker molecules from said carrier particles; and
ii) detecting aggregation of said signal particles Preferably, the analyte is an enzyme. The enzyme may degrade the carrier particle by destabilizing the surface layer. Preferably, the enzymatic activity of the enzyme creates a hole or pore in the surface layer of the carrier particle through which the linker molecules are released. Preferably said enzyme is a lipase, more preferably a phospholipase such as PLA$_2$.

Figure 1:
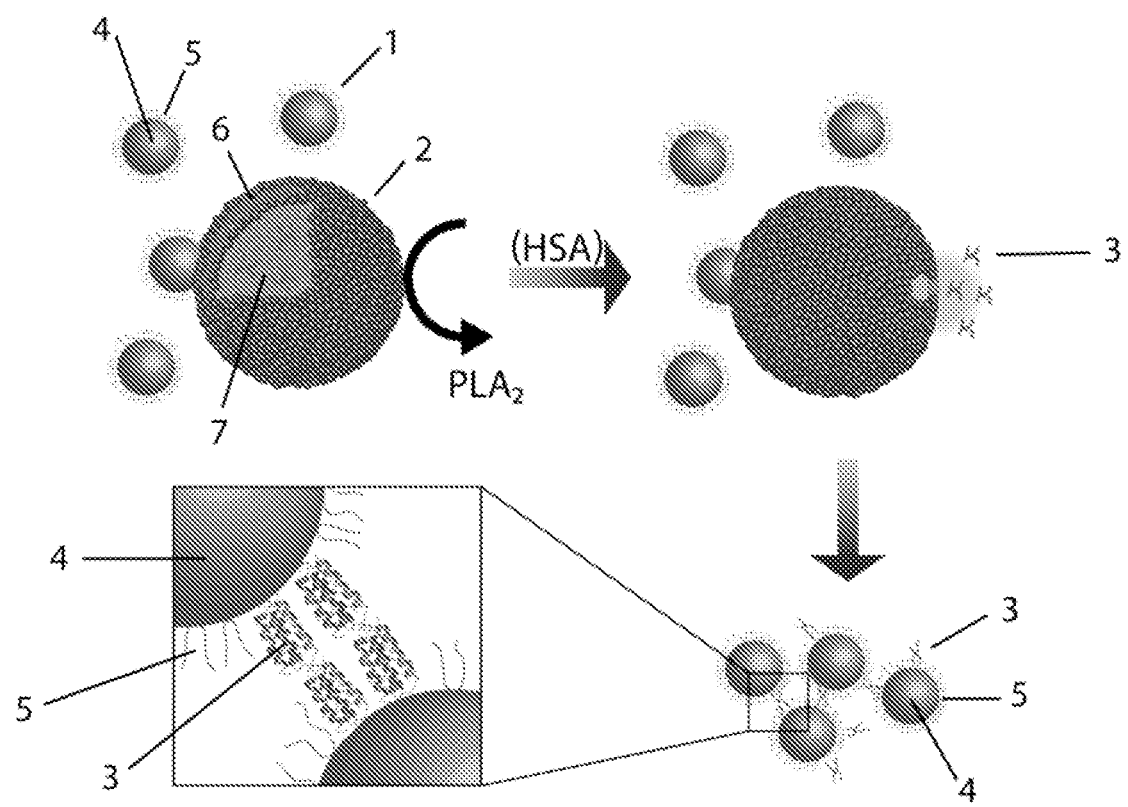

FIG. 1 illustrates one embodiment of the present invention, wherein the composition comprises a signal particle (1), a carrier particle (2) and a linker molecule (3). Said signal particle (1) comprises a core (4) on which are immobilised one or more binding moieties (5). The carrier particle (2) comprises a surface layer of amphipathic molecules (6) enclosing an interior volume (7). Addition of PLA$_2$, optionally in the presence of HSA, results in the rupture of the carrier particle (2) and release of the linker molecules (3). The linker molecules (3) then hetero-associate with the binding moieties (5) on the signal particles (1), leading to aggregation of the signal particles (1). The aggregation of the signal particles can then be detected and/or measured to provide an indication of enzymatic activity in the sample.

Preferably, the sample comprises a fluid sample. The fluid sample can be derived from any source, such as an industrial, environmental, agricultural, or biological source. The sample may comprise a synthesized or manufactured sample. Alternatively, the sample may comprise a body fluid. The sample may be derived from or consist of a physiological source including blood, serum, plasma, interstitial liquid, saliva, sputum, ocular lens liquid, sweat, urine, milk, ascots liquid, mucous, synovial liquid, peritoneal liquid, transdermalexudates, pharyngeal exudates, bronchoalveolar lavage, tracheal aspirations, cerebrospinal liquid, semen, cervical mucus, vaginal or urethral secretions and amniotic liquid. The fluid sample may be derived from a semi-solid or solid source by dilution, treatment or extraction into an aqueous liquid.

In one embodiment, the method is carried out in the presence of molecules designed to enhance the rate of enzymatic degradation of the surface layer of the carrier particle, or molecules designed to enhance the rate of carrier particle leakage. For example, the solution may additionally comprise albumin such as human serum albumin (HSA) or bovine serum albumin (BSA). As previously discussed, it has been found that the presence of HSA increases the rate of release of the linker molecules from the carrier particles. Thus, the method of the sixth aspect preferably comprises the additional step of adding albumin after contacting the sample with the composition according to the first aspect of the present invention.

Preferably, the aggregation of the signal particles is detectable through a measurable change in the system. The measurable change in the system may comprise a change in optical absorption, optical scattering, fluorescence intensity or emission peak, luminescence, optical extinction, magnetic properties, electrochemical potential, surface charge, viscosity, diffusion kinetics or optical polarisation.

A change in fluorescence can be measured using a fluorimeter. However, many biologically relevant solutions contain molecules that are either themselves fluorescent, or that alter the fluorescent yield of low molecular weight organic dyes. As described in Example 6, the presence of serum proteins in a sample markedly decreases the fluorescence signal obtained using assays based on the fluorescent dye carboxyfluorescein (CF). Thus, the measurement of a change in fluorescence may have limited use.

A more preferred measurable change comprises a change in optical absorption. The change in absorption may comprise a change in the shape of the absorption profile of the composition, such as a shift in the absorption peak. Preferably, the change in absorption occurs within the visible range of the electromagnetic spectrum. Such changes can be quantified using a number of methods. For example, a ratiometric analysis method involves the calculation of a ratio between the absorption at two particular wavelengths (e.g. 520 nm and 570 nm). Alternatively, in a peak position analysis method, the wavelength of the absolute maximum of the absorption peak can be taken as indicative of the degree of aggregation. Peak shift ($\Delta\lambda_{max}$) is a measure of the change in the wavelength of the extinction maximum in the UV-visible spectrum and is calculated by subtracting the wavelength of the maximum extinction in spectrum recorded at time point T=0 from the wavelength of the maximum extinction in spectra recorded after this time point. As described in Example 2, a ratiometric analysis method is preferred as it provides less noisy results and finer separation of low-level signals.

Such changes in optical absorption can be detected and measured using colourimetric techniques. For example, quantitative measurements can be made using a spectrometer, whilst qualitative measurements can be made by comparing the colour of the solution by eye against certain standards. Alternatively, measurements could be made by applying a mixture of the sample and composition according to the first aspect of the present invention onto a solid substrate, such as paper, plastic, nitro cellulose membrane or a thin layer chromatography plate[25].

Figure 2:
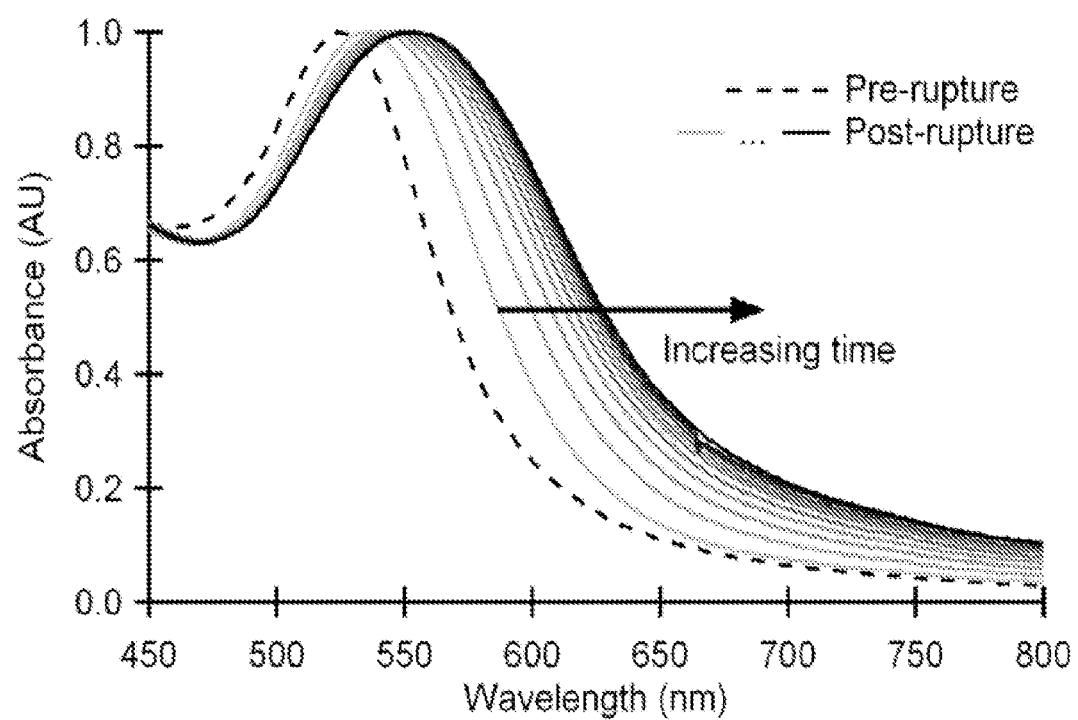
FIG. 2 shows a typical change in the absorption spectrum of a composition of the present invention as a result of signal particle aggregation, both prior to rupture of the carrier particles ( - - - ) and after rupture of the carrier particles (———).

FIG. 2 illustrates a typical change in the absorption spectrum of a composition of the present invention as a result of signal particle aggregation. Prior to liposome rupture, the linker molecules and nanoparticles are completely separated and the Plasmon absorption peak is at 520 nm, typical of a dispersed nanoparticle solution. The addition of an enzyme such as $PLA_2$ (7 nM) releases the trapped linker molecule and causes extensive nanoparticle aggregation. Within a few minutes, this aggregation induces a dramatic red-shift of the wavelength of the absolute maximum of the absorption peak to 570 nm.

The extent of the change in the system can be used to measure the concentration of the analyte in a sample or the analyte activity in a sample. In the absence of the analyte, the surface layer of the carrier particles will remain intact, the linker molecules will not be released and the signal particles will fail to aggregate. In the presence of the analyte, the carrier particles will degrade and release the linker molecules, resulting in aggregation of the signal particles. The greater the concentration of the analyte present, the more carrier particles will be degraded, the more linker molecules will be released, the greater the extent of the aggregation of the signal particles, and the greater the extent of the change in the system. In accordance with known methods, a standard curve can be produced to allow the determination of the analyte concentration or analyte activity for a given change in the system. As described in Example 5, FIG. 4 shows a calibration curve of nanoparticle spectral shift magnitudes as a function of enzyme concentration after 30 minutes of incubation with $PLA_2$. As described in Example 14, FIG. 13d shows the sigmoidal response of the assay as a function of enzyme concentration after 10 minutes of incubation with $PLA_2$ and HSA.

It has also been observed that, upon contacting the sample with the composition according to the first aspect of the present invention, there is usually a delay before aggregation of the signal particles is detected (see Example 11). This delay is known as the "lag phase" or "lag time". It has been hypothesized that the lag phase is due to an accumulation of hydrolysis products in the bilayer, especially fatty acids. Fatty acid molecules have a tendency to form segregated domains in lipid bilayers to which $PLA_2$ binds with a higher affinity. The sudden burst at the end of the lag phase may be related to a relief of local product inhibition caused by the accumulation of hydrolysis products close to the surface bound enzyme. An increase in the amount of membrane-bound $PLA_2$ has also been observed to coincide with the onset of the rapid hydrolysis at the end of the lag phase. As described in Example 12 (section i), the length of the lag phase correlates with the concentration of $PLA_2$ in the sample. In particular, a log-linear dependence has been demonstrated between the length of the lag phase and the concentration of $PLA_2$. Thus, measurement of the length of the lag phase provides an alternative method by which the concentration or activity of an analyte such as $PLA_2$ in a sample can be measured. Measurement of the length of the lag phase can also be used to screen for inhibitors, which have the effect of increasing the length of the lag phase, as described in Example 16.

The large number of parameters affecting the length of the lag phase further offers numerous possibilities to tune the dynamic range of the assay by, for example, varying the relative concentrations of the assay components.

Measurement of the length of the lag phase gives highly repeatable results on a relatively short timescale, and such methods are therefore appropriate for many routine applications. However, where the highest sensitivity is required, measurement of the extent of the change in the system e.g. the ultimate colorimetric response after 10 or 30 minutes, for example, is preferable in view of the longer incubation period.

The method of the sixth aspect of the present invention is particularly advantageous for a number of reasons. The use of carrier particles such as liposomes allows the investigation of enzymes acting on a biologically relevant substrate. Such a method is highly suitable for the detection of phospholipases such as $PLA_2$. Because of the sensitivity of $PLA_2$ to subtle changes in substrate organisation and chemistry, it is advantageous to have an assay based on interactions with unmodified phospholipids such as the phospholipid bilayers of liposomes.

The use of an assay involving the triggered release of linker molecules from carrier particles is also extremely flexible. The method can be adapted to a wide range of enzymes, as the enzymatic substrate (the surface layer of the carrier molecule) can be changed without any alteration to the principle of transduction.

As demonstrated in Example 5, the assay is very sensitive, and enables the detection of less than 10 nM $PLA_2$ after only 5 minutes of enzymatic action on the liposomes. This sensitivity is due, at least in part, to the amplification of the signal, because the degradation of a single carrier particle releases a large number of linker molecules, resulting in the aggregation of a large number of signal particles. To allow very high sensitivity measurements, it is possible to increase the reaction time. For example, as demonstrated in Example 8, the assay can be used to detect enzyme concentrations as low as 70 pM with extended incubation. Whilst the assay can be carried out at room temperature (16-25° C.), using the assay at elevated temperatures (for example, 37° C.) can decrease the reaction time and increase the sensitivity of the assay.

Because the enzymatic substrate is not chemically linked to the signal particle-linker molecule conjugate, the decoupling of the enzymatic and signal components can be utilized to tailor the assay to a desired concentration range without altering the substrate chemistry, temperature, solution conditions or incubation time. The sensitivity of the assay can be tuned from the picomolar to the micromolar level by altering the concentration of carrier particles in the assay composition, the concentration of linker molecules loaded in the carrier particles or the ratio of nanoparticles to liposomes. The release rate can be tuned by, for example, altering the loading rate of the peptide in the liposomes.

The use of linker molecules to aggregate signal particles offers a highly specific and robust transduction mechanism. The assay is capable of functioning under a wide range of solution conditions, and can function in defined medium, 10% human serum, or even whole cell lysate. This is in contrast to many prior art assay methods for which the presence of molecules such as serum proteins results in marked decrease in the signal produced.

In addition, the claimed assay method requires relatively few steps and straightforward mixing protocols, which ensures that the method is simple and easily automated.

As discussed above, the dysregulation of enzymes is implicated in a huge variety of diseases and conditions. Depending on the disease or condition in question, the pathology may result from, or be associated with, an abnormally high or an abnormally low concentration of the enzyme, or abnormally high or abnormally low enzymatic activity. The dyregulation of the enzyme may be the cause of the disease, or may simply be indicative of pathology such as localized inflammation. The measurement of enzyme concentration or of enzymatic activity in a sample can therefore be used to diagnose such diseases. The seventh aspect of the present invention provides a method of diagnosing a disease or condition associated with dysregulation of an enzyme in a subject comprising the steps of:
  i) contacting a sample from said subject with the composition according to the first aspect of the present invention, wherein said enzyme degrades said carrier particles, releasing said linker molecules from said carrier particles; and
  ii) detecting aggregation of said signal particles.

The aggregation of said signal particles can be detected and measured as previously discussed in relation to the sixth aspect.

The extent of the aggregation of the signal particles is directly correlated with the enzyme concentration or enzymatic activity in the sample. The extent of aggregation (assessed though the measurable change) can be compared with the extent of aggregation produced by a 'normal' enzyme concentration (e.g. the average enzyme concentration in a healthy subject) in order to determine whether the enzyme concentration or enzymatic activity is abnormally high or abnormally low. Any deviation from the normal enzyme concentration or activity can be used by one of skill in the art to diagnose a disease or condition associated with dysregulation of the enzyme.

The enzyme in question may be, for example, a lipase, phospholipase or triacylglycerol lipase. Phospholipases include phospholipase A1, phospholipase A2, phospholipase B, phospholipase C, phospholipase D1 and phospholipase D2. Triacylglycerol lipases include pancreatic lipase, gastric lipase and lingual lipase. Other enzymes of interest include diacylglycerol lipase, cholesterase, sphingomyelin phosphodiesterases, hepatic lipase, endothelial lipase, lipoprotein lipase, bile salt dependent lipase, and hormone-sensitive lipase.

As previously mentioned, an enzyme of particular interest is $PLA_2$. The concentration of $PLA_2$ is indicative of a number of diseases and conditions, including atherosclerosis, pancreatitis, acute sepsis and cancer. Therefore, the seventh aspect of the present invention preferably provides a method of diagnosing atherosclerosis, pancreatitis, acute sepsis or cancer.

In addition to studying enzyme levels for diagnostic purposes, another important application of enzymatic assays is high-throughput screening for agents that modulate the activity of the enzyme. Thus, the eighth aspect of the present invention provides a method for screening for a modulator of enzymatic activity comprising the steps of:
  i) contacting the enzyme with a test substance or test mixture and the composition according to the first aspect of the present invention; and
  ii) detecting aggregation of said signal particles.

The aggregation of said signal particles can be detected and measured as previously discussed in relation to the sixth aspect.

The extent of aggregation (assessed though the measurable change) can be compared with the extent of aggregation produced in the absence of the test substance or test mixture, in order to determine whether the test substance or test mixture has increased or decreased enzymatic activity.

The test mixture may comprise a defined mixture of artificial compounds or naturally-derived samples of potentially unknown or uncharacterised composition.

The step of contacting the enzyme with the test substance/test mixture and the composition according to the first aspect of the present invention may comprise simultaneous or sequential mixing of the components. In one embodiment, the test substance/test mixture and composition according to the first aspect of the present invention may be mixed first, followed by the addition of the enzyme. The preferred mixing sequence will depend upon the components in question.

Of particular interest are potential inhibitors of enzymes. In the presence of an inhibitor, the extent of aggregation of the signal particles will be reduced in comparison to the extent of aggregation in the absence of the test substance/test mixture. Inhibitors have also been found to increase the length of the lag phase before signal aggregation is detected, as described in Example 16. The above method can be used to screen both for solution-based inhibitors and substrate-based inhibitors. When screening for a substrate-based inhibitor, such as the amphiphilic competitive inhibitor MJ33, the test substance is preferably contained within the surface layer of one or more carrier particles. These carrier particles may also contain the linker molecules, or may be a separate population of carrier particles which compete for the enzymatic activity.

The methods of the eighth aspect are extremely flexible, because the enzymatic substrate (the surface layer of the carrier particle) is not chemically linked to the signal particle-linker molecule conjugate. Whether screening for solution-based inhibitors or substrate-based inhibitors, the signal particle-based transduction is exactly the same, requiring no re-engineering of either the signal particle, the binding moieties or the carrier particle encapsulation. This flexibility allows quantitative investigation of both soluble and substrate-incorporated enzyme inhibitors.

In addition, unlike with electroactive or fluorometric systems, there is very little chance for spurious results to affect the readout mechanism rather than the enzyme, even with charged or highly conjugated inhibitors.

As described above, the release substance may also comprise a derived antimicrobial moiety, such as a peptide, which is capable of inducing permeabilisation, leakage and rupture of a membrane. The ninth aspect of the present invention therefore provides a method of screening for candidate antimicrobial peptides comprising the steps of:
  i) contacting a test substance or test mixture with the composition according to the first aspect of the present invention; and
  ii) detecting aggregation of said signal particles.

The aggregation of said signal particles can be detected and measured as previously discussed in relation to the sixth aspect.

Any significant aggregation of the signal particles will indicate that the test substance/test mixture has induced sufficient permeabilisation, leakage or rupture of the surface layer of the carrier particle to release the linker molecules, and therefore that said test substance/test mixture is or contains a candidate antimicrobial peptide. In this aspect, the carrier particle is preferably a liposome.

A number of toxins exert their damaging effects through disruption of cell membranes. For example, *Staphylococcus aureus* alpha toxin is a membrane-disrupting toxin that creates pores in membranes, resulting in hemolysis and tissue damage. *Clostridium perfringens* alpha toxin is a membrane-disrupting toxin with phospholipase C activity and is directly responsible for gas gangrene and myonecrosis. The composition of the first aspect of the present invention can therefore be used to detect or screen for such toxins through the action of the toxins on the surface layer of the carrier particle. A tenth aspect of the present invention therefore provides a method for detecting toxins comprising the steps of:
  i) contacting a test substance or test mixture with the composition according to the first aspect of the present invention; and
  ii) detecting aggregation of said signal particles.

The aggregation of said signal particles can be detected and measured as previously discussed in relation to the sixth aspect.

Any significant aggregation of the signal particles will indicate that the test substance or test mixture has disrupted or degraded the surface layer of the carrier particle to release the linker molecules, and therefore that said test substance/test mixture is or contains a toxin. This method can therefore also be used to screen for potential toxins.

Preferably, the surface layer of the carrier particle comprises lipids or phospholipids, and is sufficiently similar in composition to natural cell membranes to mimic the effect of the toxin upon animal cells.

The details of the invention provided in the detailed description and in the examples below apply mutatis mutandis to all embodiments of the present invention.

The aspects of the present invention will now be illustrated by way of the following, non-limiting examples.

EXAMPLES

Example 1

Preparation of Materials

The Polypeptides: The polypeptides JR2EC (SEQ ID NO. 1) and JR2KC (SEQ ID NO. 2), were synthesized on a Pioneer automated peptide synthesizer (Applied Biosystems) using standard fluorenylmethoxycarbonyl (Fmoc) chemistry protocols and Fmoc-Gly-poly(ethylene)glycol-polystyrene resin. The crude products were purified by reversed-phase HPLC on a semi-preparative HICHROM C-8 column and identified by MALDI-TOF mass spectrometry. In order to obtain $JR2KC_2$, lyophilized peptide monomers (1 mM) were dissolved in 0.1 M ammonium bicarbonate buffer pH 8, aerated for 90 minutes and incubated at 4° C. for at least 24 hours before use. The synthesis is described in more detail in the prior art [16].

Other Chemicals: Phosphate buffered saline (PBS), carboxyfluorescein (CF), Phospholipase $A_2$ from *Naja mossambica mossambica* and human serum albumin (HSA) were purchased from Sigma Aldrich (Dorset, UK) and used without further purification. The $PLA_2$ inhibitors chlorpromazine and MJ33 were also purchased from Sigma Aldrich. Lipids were purchased from Avanti Polar Lipids (Alabaster, Ala.).

Nanoparticles: Gold nanoparticles (20 nm) from British BioCell International (BBI) were incubated for 16 hours with 10 µM of JR2EC. The particles were repeatedly centrifuged at 15,000 G and resuspended in 30 mM Bis-Tris pH 7 in order to reduce the concentration of unbound JR2EC to <0.1 nM.

Liposomes: Polypeptide-loaded large unilamellar liposomes were prepared by extrusion, as described in the art[20]. Each batch was prepared from 5 mg of 1-palmitoyl-2-oleoyl-sn-glycero-3-phosphocholine (POPC) in chloroform at 10 mg/ml. The lipid was first dried under a stream of argon, then placed under vacuum for at least two hours to remove any residual solvent. The dried lipid film was then rehydrated in 1 ml of 0.25 mM JR2KC$_2$ in PBS (10 mM phosphate, 150 mM NaCl, pH 7.4) and vortexed. The resulting multilamellar vesicle solution was extruded 19 times through a Nucleopore polycarbonate membrane with 100 nm pores. Untrapped peptides were removed from the liposome suspension by gel filtration through a Sephadex G-100 column using PBS as eluent.

Carboxyfluorescein-loaded liposomes were prepared similarly, except that the rehydration solution was 50 mM CF, 20 mM phosphate, adjusted to pH 7 with NaOH. The untrapped dye was removed by filtration on a Sephadex G-25 column with PBS as eluent. The total lipid concentration in all samples was determined using the Stewart assay.[21]

These materials were used, as appropriate, in the following examples.

Example 2

Comparison of Ratiometric and Peak Position Data Analysis Methods

Methodology: JR2EC-functionalised nanoparticles (0.1 nM) and JR2KC$_2$-loaded liposomes (5 mg/ml phospholipid), prepared in accordance with Example 1, were suspended in phosphate buffered saline (PBS) pH 7.4 with 0.5 mM Ca$^{2+}$. The nanoparticle-liposome mixture was treated with PLA$_2$ and HSA (4 mg/ml). For each sample, the following concentrations of PLA$_2$ were used:
(i) 500 ng/ml;
(ii) 250 ng/ml;
(iii) 100 ng/ml;
(iv) 25 ng/ml.

UV-visible spectra were recorded on a Perkin Elmer Lambda 25 UV-Vis Spectrophotometer. The resulting absorption spectra collected over time were analysed using two different methods:
(a) Ratiometric Analysis Method In this method, a ratio between the absorption at 520 nm and 570 nm (the plasmon shift) is calculated using Equation 1:

$$\Delta = \frac{(A_{agg} - A_{abs})}{A_{disp} - A_{abs}} \quad \text{(Equation 1)}$$

where $A_{agg}$ is the absorption due to aggregated particles (measured at 570 nm), $A_{disp}$ is the absorption due to dispersed particles (measured at 520 nm) and $A_{scat}$ is the absorption due to scattering (normalized at 800 nm).
(b) Peak Position Analysis Method In this method, the wavelength of the absolute maximum of the absorption peak is taken as indicative of the degree of aggregation.

Results: The data obtained using each method is shown in FIG. 6. The lines show the data obtained using the ratiometric technique (a), whilst the points show the data obtained using the peak position analysis method (b). The ratiometric method not only gave less noisy results, but also finer separation of low-level signals.

Example 3

Stability of Peptide-Loaded Liposomes

Methodology: Liposomes composed of 1-palmitoyl-2-oleoyl-sn-glycero-3-phosphocholine (POPC) were prepared by extrusion of 5 mg/ml POPC in PBS buffer (10 mM phosphate, 140 mM NaCl, pH 7.4) through a polycarbonate membrane with 100 nm pores. The resulting liposomes had a narrow size distribution with an average hydrodynamic radius ($R_H$) of 49±2 nm as measured by dynamic light scattering and a zeta potential ($\zeta$) of −6.6±0.4 mV. The negative zeta potential of these zwitterionic POPC liposomes is in good agreement with previously reported[27]

For preparation of peptide-loaded liposomes, the lipids were rehydrated and extruded in PBS containing 0.25 mM of JR2KC$_2$, as described in Example 1. Untrapped peptides were removed using a Sephadex G100 gel filtration column. The hydrodynamic radius and zeta-potential of the peptide-loaded liposomes were 51±6 nm and −7.6±1.2 mV, respectively. These values are not significantly different from the liposomes containing only buffer, indicating that the peptides were not extensively associated with the outer leaflet of the lipid membrane.

CF-loaded liposomes were prepared in accordance with the method in Example 1.

Results: Both the liposomes and their peptide cargo demonstrated a remarkable stability during storage. Even after 4 weeks at 4° C., the liposome solution induced no nanoparticle aggregation in the absence of PLA$_2$, indicating that the peptide had not leaked from the liposome interior. However, upon addition of 0.1 vol % of the detergent Triton X100 to the nanoparticle-liposome mixture, the nanoparticles exhibited a dramatic 40 nm red-shift of the plasmon band, showing that the peptide-liposome system remained intact and active.

This stability was not shared by the more conventional CF release assay, as significant background leakage occurred during storage. In only 24 hr at 4° C., the CF-loaded liposomes released 15% of their contents, demonstrating that the peptide-liposome system exhibits significantly better stability. The slower release of the JR2KC$_2$ (SEQ ID NO. 2) is likely due to the fact that the polypeptide is significantly larger than CF. The peptide also has many more polar and charged groups than CF, which increases the energetic barrier for crossing the hydrophobic bilayer core. In fact, the liposome system was so effective at retaining the polypeptide that, in this particular example, addition of PLA$_2$ alone released only very small amounts of the peptide, insufficient to induce significant nanoparticle crosslinking.

Example 4

The Effect of Solution Conditions on Assay Performance

Methodology: Mixed solutions of 20 nm JR2EC-functionalised gold nanoparticles and 100 nm JR2KC$_2$-loaded liposomes were prepared in accordance with Example 1. Absorption spectra were measured for the solutions under various solution conditions, as discussed below.

Figure 3:
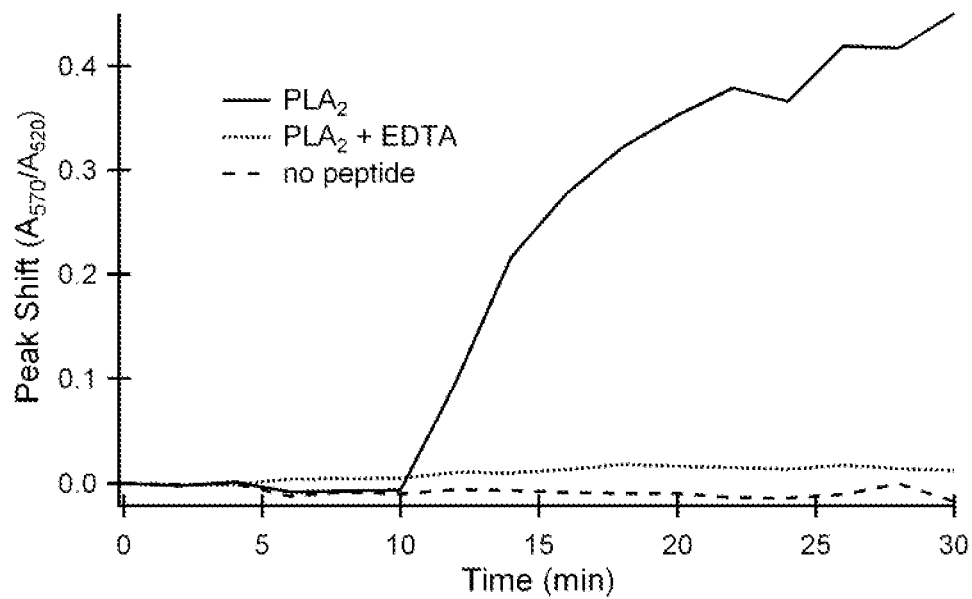
FIG. 3 shows a plot of peak shift (calculated as the ratio of absorption of a composition of the present invention at 570 nm and 520 nm) over time under a number of different solution conditions at room temperature.
Figure 3:
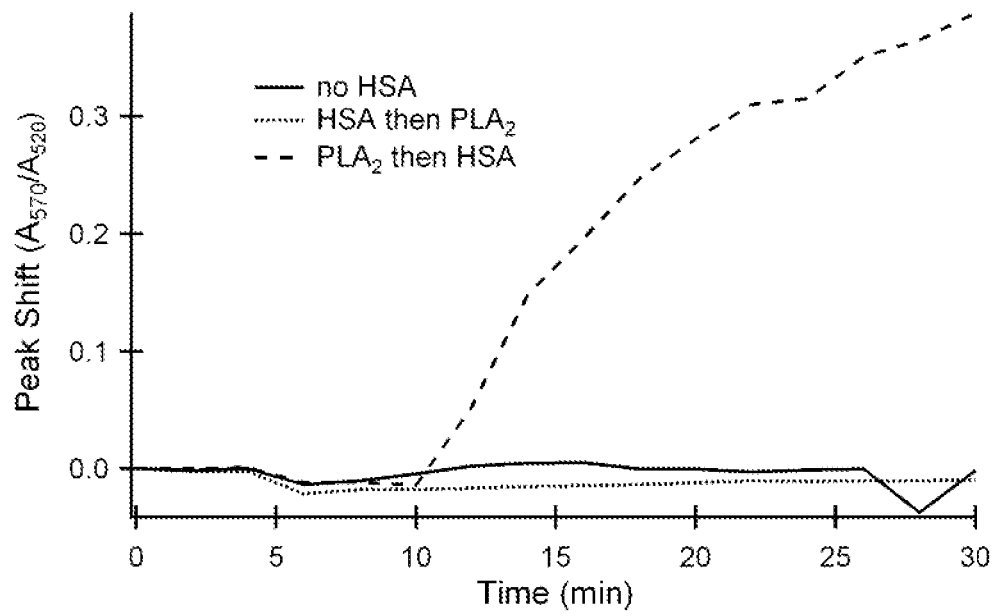

As shown in FIG. 3A, the absorption spectra were measured:
(i) in the presence of PLA$_2$;
(ii) in the presence of PLA$_2$ and EDTA; and
(iii) in the absence of the peptide linker molecule.

Results (A): Upon liposome cleavage by the enzyme PLA$_2$, the trapped peptide was released, causing the nanoparticle absorption spectrum to red shift. A plot of the ratio of absorption at 570 and 520 nm reveals this shift. The phospholipase used in this study is calcium-dependent. As expected, inclusion of EDTA in the medium prevented aggregation, presumably by inhibiting enzymatic liposome degradation. The addition of PLA$_2$ also induced no aggregation when no peptide linker molecule was included in the liposomes, demonstrating that the enzyme itself is not directly responsible for the observed spectral shift.

As shown in FIG. 3B, absorption spectra were also measured:
(i) in the absence of HSA;
(ii) when addition of PLA$_2$ followed the addition of HSA; and
(iii) when the addition of HSA followed the addition of PLA$_2$.

HSA is a ubiquitous protein in serum that, among other roles, transports fatty acids to the liver.

Results (B): It has been found that the addition of human serum albumin (HSA) after incubation of the liposomes with PLA$_2$ greatly increases the rate of release of the linker molecule from the carrier particle. The addition of 4 mg/ml of HSA to the peptide-loaded liposomes immediately (30 seconds) after addition of PLA$_2$ led to a rapid release of the peptides and extensive particle aggregation. HSA alone did not cause any particle aggregation. Interestingly, addition of HSA before PLA$_2$ prevented release of the peptides, suggesting that binding of HSA to the liposomes may hinder the association of PLA$_2$ with the liposomes. As described above, control experiments shown in FIG. 3A using blank liposomes (without the peptide linker molecule) resulted in no nanoparticle crosslinking. Similarly, experiments performed in the absence of Ca$^{2+}$ gave no crosslinking, as the $PLA_2$ used is $Ca^{2+}$-dependent. We can thus attribute the aggregation of the JR2EC-modified nanoparticles to the $PLA_2$-dependent release of $JR2KC_2$, assisted by the presence of HSA.

Example 5

Quantitative Performance of the Assay

After optimizing and verifying the behavior of the system, the quantitative performance of the assay was determined.

Methodology: A composition comprising JR2EC-functionalised nanoparticles (0.1 nM) and $JR2KC_2$-loaded liposomes (5 mg/ml phospholipid) was prepared in accordance with Example 1. The composition was incubated for 30 minutes with a solution of $PLA_2$ at a variety of concentrations. The nanoparticle absorption spectrum was analyzed using Equation 1:

$$\Delta = \frac{(A_{agg} - A_{abs})}{A_{disp} - A_{abs}} \quad \text{(Equation 1)}$$

where $A_{agg}$ is the absorption due to aggregated particles (measured at 570 nm), $A_{disp}$ is the absorption due to dispersed particles (measured at 520 nm) and $A_{scat}$ is the absorption due to scattering (normalized at 800 nm).

Results: The response obtained was found to depend primarily on the quantity of $PLA_2$ added and the amount of time for which this enzyme is incubated with the liposomes. Incubation time with HSA was not an important factor, since the response after addition of HSA was almost immediate. The assay enabled detection of less than 10 nM $PLA_2$ after only 5 minutes of enzymatic action on the liposomes. The results for a range of enzyme concentrations are given in FIG. 4. The maximum shift intensity is plotted ±SEM for each point. The results show a sigmoidal response with concentration. Given these conditions (nanoparticle concentration of 0.3 nM, peptide loading concentration of 0.5 mM and liposome concentration of 0.1 mg/ml) the lower limit of detection was approximately 1 nM. The upper limit of quantitation was around 50 nM due to the fact that, at high $PLA_2$ levels, the peptide linker molecule was concentrated enough to saturate the nanoparticles, thus reducing the extent of aggregation. However this range is tunable, as altering the concentration of liposomes used or the concentration of linker molecules loaded in the liposomes will shift the response curve. Thus, without altering the substrate chemistry, temperature, solution conditions or incubation time, it is possible to tailor the assay to a desired concentration range.

Example 6

Effect of Serum Proteins on Traditional Carboxyfluorescein-Based Assay

Methodology: A 0.75 μM solution of carboxyfluorescein (CF) in PBS was prepared. The fluorescence emission was first measured as a function of wavelength for this solution (·········). Spectra were then collected after the sequential addition of 30 μM HSA ( - - - ) and 0.17 mM Triton X-100 (——).

Results: As shown in FIG. 5, addition of HSA to a CF solution altered the emission profile of that dye. Although the maximum peak position was not altered, the peak intensity was changed significantly. HSA decreased the CF emission by nearly a third, while HSA and Triton X-100 acted cooperatively to decrease emission by nearly two thirds. The addition of Triton X-100 alone had no effect on emission intensity (data not shown).

Thus, the presence of serum proteins markedly decreases the fluorescent signal obtained using the traditional CF-based assay. Further complicating the situation is the fact that the detergent added to lyse the vesicles and calibrate the system acts cooperatively with the proteins to additionally decrease the fluorescence yield. Although these effects can be compensated for a given protein level, doing so in a clinical assay would necessitate the added step of measuring protein levels in each sample. It is also not clear that the effect would be the same given different ratios of the many proteins commonly found in biological samples. Thus, the stability and adaptability of the traditional CF-based assay is limited.

Example 7

Response from Carboxyfluoresceine Assay as a Function of Enzyme Concentration The response from the prior art carboxyfluorescein (CF) release assay as a function of enzyme concentration was investigated.

Methodology: Liposomes containing 50 mM of carboxyfluorescein were prepared as described in Example 1. The final lipid concentration in the sample was 30 μg/ml. The liposomes were incubated with solutions of $PLA_2$ at a variety of concentrations for 30 minutes. Experiments were performed on a Perkin Elmer fluorimeter with an excitation wavelength of 490 nm and an emission wavelength of 520 nm. Slit widths of 10 nm were used in both cases. All experiments were performed at 22° C., as maintained by a constant temperature bath. Control experiments in which the liposomes were ruptured with Triton X-100 established the maximum response.

Results: The results are shown in FIG. 7. The release was linearly dependent on the concentration PLA$_2$ and enabled detection at a lower level of 1 nM. Under the conditions investigated, 200 nM PLA$_2$ was sufficient to rupture nearly all of the liposomes in 30 min.

Example 8

Sensitivity of the Assay

The sensitivity of the assay of the present invention was tested using extended incubation times.

Methodology: A composition comprising JR2EC-functionalised nanoparticles (0.1 nM) and JR2KC$_2$-loaded liposomes (5 mg/ml phospholipid) was prepared in accordance with Example 1. This solution was incubated at room temperature with 70 pM solution of PLA$_2$ for 12 hours. An identical solution was incubated in the absence of PLA$_2$. HSA was then added to both solutions and, 20 minutes later, optical absorption was measured.

Results: The data obtained are shown in FIG. 8. The solid lines (——) show the optical extinction of the solution incubated with PLA$_2$, whilst the dashed lines ( - - - ) show the optical extinction of the solution incubated in the absence of PLA$_2$. The results indicate that the present assay can be used to detect enzyme concentrations as low as 70 pM with extended incubation. By optimizing reaction conditions, it is likely possible to move this detection limit even lower.

Example 9

Effect of PEG-Grafted Lipids

The effect of providing a liposome comprising a surface layer containing PEG-grafted lipids was investigated.

Methodology: Liposomes comprising 1.5 mol % PEG-lipids were prepared. Optical absorption was measured (i) before the addition of PLA$_2$ and (ii) 8 minutes after the addition of 0.7 nM PLA$_2$. No HSA was added.

Results: The data obtained are shown in FIG. 9. The solid lines (——) show the optical extinction of the solution before the addition of PLA$_2$ and the dashed lines ( - - - ) show the optical extinction of the solution after the addition of PLA$_2$. Liposomes containing 1.5 mol % of PEG-lipids gave a significantly larger redshift of the plasmon peak without the need for HSA.

Example 10

Stability of Peptide-Loaded Liposomes II

Methodology: JR2EC-functionalised nanoparticles and JR2KC$_2$-loaded liposomes, prepared in accordance with Example 1, were suspended in phosphate buffered saline (PBS) pH 7.4 with 0.5 mM Ca$^{2+}$. The JR2KC$_2$-loaded liposomes were diluted to a total lipid concentration of 0.1 mg/ml. The concentration of JR2KC$_2$ loaded into the liposomes was 0.25 mM, which would yield a concentration of about 0.1 μM of JR2KC$_2$ in the event of 100% release. The liposomes were stored for 15 weeks at 4° C., dispersed in PBS buffer in an eppendorf tube. The liposomes were stored in the dark, but were not protected from mechanical vibration or occasional exposure to light. 1.4 nM of PLA$_2$ was added and the assay response was measured spectroscopically (in the UV-visible range) by recording full spectra in the range 400-800 nm at 2 minute intervals for 30 minutes using a Perkin Elmer Lambda 25 Spectrophotometer. Peak shift ($\Delta\lambda_{max}$; the change in the wavelength of the extinction maximum in the UV-visible spectrum) was obtained by subtracting the wavelength of maximum extinction ($\lambda_{max}$) before addition of PLA$_2$ from the $\lambda_{max}$ after addition of PLA$_2$. Unless otherwise stated, all measurements were performed at room temperature (approximately 25° C.).

Controls were also performed: i) in the absence of Ca$^{2+}$ and: ii) using nanoparticles functionalised with a modified form of JR2EC in which L-alanines are replaced with D-alanines, rendering the peptide unable to fold and form the heterotrimeric complex.

Results: At this concentration of JR2KC$_2$ an extensive aggregation of the JR2EC modified signal particles is induced. As shown in FIG. 10a, when exposed to PLA$_2$, the degradation of the liposomes resulted in a release of the entrapped JR2KC$_2$ peptides that induced a significant redshift of the localized surface plasmon resonance (LSPR) band of the gold nanoparticles. This rapid transduction and large optical shift enabled real-time monitoring of the enzymatic activity. The peptide loaded liposomes exhibited a remarkable stability. No detectable background leakage of JR2KC$_2$ was observed after 15 weeks of storage, whereas a large response was obtained after the addition of 7 nM PLA$_2$ (see FIG. 11a). The data indicate that there was no spontaneous release of JR2KC$_2$ in the absence of PLA$_2$ whilst the liposomes retained full responsiveness towards PLA$_2$.

Because the catalytic activity of the PLA$_2$ used here (*naja mossambica mossambica*) is highly dependent on the presence of millimolar concentrations of Ca$^{2+}$, repeating the experiments in the absence of Ca$^{2+}$ is a useful negative control. As expected, no particle aggregation was observed in the absence of Ca$^{2+}$ upon addition of PLA$_2$ (see FIG. 10b). This observation confirms that the aggregation of the particles is dependent on the PLA$_2$-mediated hydrolysis of the lipids, rather than simply the presence of the enzyme. Moreover, the particles coated with the modified, non-folding JR2EC peptide did not aggregate upon PLA$_2$-mediated release of JR2KC$_2$ (see FIG. 10b).

Example 11

Lag Phase

Methodology: JR2EC-functionalised nanoparticles (0.1 nM) and JR2KC$_2$-loaded liposomes (5 mg/ml phospholipid), prepared in accordance with Example 1, were suspended in phosphate buffered saline (PBS) pH 7.4 with 0.5 mM Ca$^{2+}$. 1.4 nM of PLA$_2$ was added. The assay response was measured spectroscopically (in the UV-visible range) by recording full spectra in the range 400-800 nm at 2 minute intervals for 60 minutes using a Perkin Elmer Lambda 25 Spectrophotometer. PLA$_2$ was added at time point T=5 minutes. Peak shift ($\Delta\lambda_{max}$) was obtained by subtracting the wavelength of maximum extinction ($\lambda_{max}$) before addition of PLA$_2$ from the $\lambda_{max}$ after addition of PLA$_2$.

Results: Addition of 1.4 nM of PLA$_2$ did not induce an immediate particle aggregation but rather showed a lag-burst behaviour i.e. a lag phase followed by a short burst phase (see FIG. 10b). This indicates that the release of JR2KC$_2$ is preceded by a concentration-dependent lag phase.

Example 12

Effect of Analyte Concentration and Temperature on Lag-Phase

The duration of the lag phase is an important kinetic parameter that depends on the concentration and activity of phospholipase in the sample. With this in mind, a systematic investigation was performed to determine whether the lag time could be used as an appropriate assay metric.

Materials: JR2EC-functionalised nanoparticles (0.1 nM) and JR2KC$_2$-loaded liposomes (0.1 mg/ml phospholipid), prepared in accordance with Example 1, were suspended in phosphate buffered saline (PBS) pH 7.4 with 0.5 mM Ca$^{2+}$.

i) Effect of Analyte Concentration

Methodology: PLA$_2$ was added in the following concentrations; i) 7 nM ii) 3.5 nM iii) 1.4 nM or iv) 700 pM. The assay response was measured spectroscopically (in the UV-visible range) by recording full spectra in the range 400-800 nm at 2 minute intervals for 60 minutes using a Perkin Elmer Lambda 25 Spectrophotometer, at 37° C. PLA$_2$ was added at time point T=5 minutes. Peak shift ($\Delta\lambda_{max}$) was obtained by subtracting the wavelength of maximum extinction ($\lambda_{max}$) before addition of PLA$_2$ from the $\lambda_{max}$ after addition of PLA$_2$.

Results: The length of the lag phase was found to be clearly dependent on the concentration of PLA$_2$, and spanned from 5 to 40 minutes for concentrations ranging from 7 nM-700 pM (see FIG. 12a) in the presence of 0.5 mM Ca$^{2+}$ at 37° C.

ii) Effect of Temperature

Methodology: 7 nM PLA$_2$ was added under the following conditions: i) room temperature and ii) 37° C. The assay response was measured spectroscopically (in the UV-visible range) by recording full spectra in the range 400-800 nm at 2 minute intervals for 60 minutes using a Perkin Elmer Lambda 25 Spectrophotometer. PLA$_2$ was added at T=5 minutes. Peak shift ($\Delta\lambda_{max}$) was obtained by subtracting the wavelength of maximum extinction ($\lambda_{max}$) before addition of PLA$_2$ from the $\lambda_{max}$ after addition of PLA$_2$.

Results: As shown in FIG. 13a, temperature also had a significant influence on the length of the lag phase. At a concentration of 7 nM PLA$_2$, the lag period at room temperature was about 20 minutes longer than it was at 37° C.

Example 13

Effect of Human Serum Albumin on Assay Performance

Methodology: JR2EC-functionalised nanoparticles (0.1 nM) and JR2KC$_2$-loaded liposomes (0.1 mg/ml phospholipid), prepared in accordance with Example 1, were suspended in phosphate buffered saline (PBS) pH 7.4 with 0.5 mM Ca$^{2+}$. 7 nM PLA$_2$ was added under the following conditions: i) with the addition of 4 mg/ml of Human Serum Albumin (HSA) to the peptide-loaded liposomes 5 minutes after addition of PLA$_2$ and ii) without the addition of HSA. The assay response was measured spectroscopically (in the UV-visible range) by recording full spectra in the range 400-800 nm at 2 minute intervals for 30 minutes using a Perkin Elmer Lambda 25 Spectrophotometer. PLA$_2$ was added at time point T=5 minutes. Peak shift ($\Delta\lambda_{max}$) was obtained by subtracting the wavelength of maximum extinction ($\lambda_{max}$) before addition of PLA$_2$ from the $\lambda_{max}$ after addition of PLA$_2$.

The experiment was repeated using 4 mg/mL of HSA and 70 nM PLA$_2$ at room temperature, and controls were performed i) in the absence of Ca$^{2+}$ and ii) in the absence of JR2KC$_2$.

Results: The addition of the HSA to the peptide-loaded liposomes led to an almost immediate release of the peptides and extensive particle aggregation (see FIG. 13b). HSA alone did not cause any particle aggregation. Similarly, as shown in FIG. 13c, addition of HSA after PLA$_2$ in the absence of Ca$^{2+}$ failed to induce aggregation, as did the use of liposomes not loaded with JR2KC$_2$. We therefore hypothesize that HSA binds to the liposome surface and removes the fatty acids that have accumulated in the membrane, as a result of enzymatic hydrolysis of the phospholipid, destabilizing the liposomes and resulting in a more rapid lysis. The shift of the plasmon peak is also larger in the presence of HSA, indicating that the presence of a high concentration of fatty acids may interfere with the association and folding of the polypeptides.

Example 14

Effect of PLA$_2$ Concentration on Assay Performance

Methodology: JR2EC-functionalised nanoparticles (0.1 nM) and JR2KC$_2$-loaded liposomes (0.1 mg/ml phospholipid), prepared in accordance with Example 1, were suspended in phosphate buffered saline (PBS) pH 7.4 with 0.5 mM Ca$^{2+}$. The assay response was measured spectroscopically (in the UV-visible range) by recording full spectra in the range 400-800 nm 10 minutes after the addition of 4 mg/mL HSA for a variety of PLA$_2$ concentrations, using a Perkin Elmer Lambda 25 Spectrophotometer. Peak shift ($\Delta\lambda_{max}$) was obtained by subtracting the wavelength of maximum extinction ($\lambda_{max}$) before addition of PLA$_2$ from the $\lambda_{max}$ after addition of PLA$_2$.

Results: The results for a range of enzyme levels are given in FIG. 13d and show a sigmoidal response with concentration. The response of the assay depended primarily on the quantity of active PLA$_2$ present in the sample and the amount of time for which this enzyme is incubated with the liposomes. Using HSA, it was possible to detect less than 10 nM PLA$_2$ after only 5 minutes of enzymatic action at room temperature.

Example 15

Effect of PEG-Grafted Lipids on Lag-Time

Methodology: JR2KC$_2$-loaded liposomes with 2% 1,2-dioleoyl-sn-glycero-3-phosphoethanolamine-N-[methoxy(polyethylene glycol)] (PEG, molecular weight=4000 g/mol) and JR2EC-functionalised nanoparticles (0.1 nM), prepared in accordance with Example 1 were suspended in phosphate buffered saline (PBS) pH 7.4 with 0.5 mM Ca$^{2+}$. The assay response was measured spectroscopically (in the UV-visible range) by recording full spectra in the range 400-800 nm at 2 minute intervals for 30 minutes using a Perkin Elmer Lambda 25 Spectrophotometer, at room temperature, with and without the addition of PLA$_2$. Peak shift ($\Delta\lambda_{max}$) was obtained by subtracting the wavelength of maximum extinction ($\lambda_{max}$) before addition of PLA$_2$ from the $\lambda_{max}$ after addition of PLA$_2$.

Results: In the PEG-grafted liposomes a significantly faster release of the peptides was observed at room temperature (see FIG. 11b). The lag time decreased from about 25 minutes in POPC liposomes to 10 minutes with the addition of 2% PEGylated lipids. The total response was also slightly higher as compared to pure POPC liposomes.

The inclusion of lipids modified with poly(ethylene glycol) (PEG) is a common modification for drug delivery applications as it decreases non-specific interactions between the liposomes and proteins present in solution. Interestingly, in spite of this diminished non-specific interaction, the specific hydrolysis of lipids by phospholipases is actually increased in liposomes containing a small fraction of PEG-terminated lipids. This effect is most likely mediated by the negative net charge carried by the PEG-lipids.

Example 16

Effect of Inhibitors on Lag-Time

One application in which it is important to measure the activity of an enzyme rather than just its concentration is high-throughput screening for inhibitors. Chlorpromazine is a prototypical, water-soluble small molecule inhibitor of $PLA_2$ and is therefore a good test case for the utility of this assay in such screening.

Methodology: $JR2KC_2$ loaded liposomes, carboxyfluorescein (CF)-loaded liposomes and JR2EC-functionalised gold nanoparticles were prepared as described in Example 1. A mixture of $PLA_2$ and chlorpromazine was added to the suspensions of liposomes. The assay response was recorded spectroscopically (in the UV-visible range) after incubating various concentrations of chlorpromazine with $PLA_2$ (7 nM), functionalized gold nanoparticles (0.1 nM) and liposomes (1.4 nM) for 10 minutes at 37° C. For $JR2KC_2$-loaded liposomes, the assay response was measured spectroscopically (in the UV-visible range) by recording spectra in the range 400-800 nm with 2 minute intervals using a Perkin Elmer Lambda 25 Spectrophotometer, and then extracting $\Delta\lambda_{max}$.

Results: These experiments yielded an $IC_{50}$ for chlorpromazine of 6.5 µM (FIG. 14). This value was obtained by fitting the data to the monophasic Hill equation:

$$y = \min + \frac{(\max - \min)}{1 + \left(\frac{x}{IC_{50}}\right)^n}$$

where min is the fully inhibited value, max is the uninhibited value, x is the concentration of inhibitor and n is the Hill coefficient. The lag time increased from about 5 minutes without the inhibitor to approximately 15 minutes in the presence of 10 µM of chlorpromazine (see FIG. 15). This lag time indicates that the concentration of active non-inhibited $PLA_2$ was about half of the actual $PLA_2$ concentration present in the sample (see FIG. 12b).

The inhibition by chlorpromazine was confirmed using CF-loaded liposomes, which gave an $IC_{50}$ value of 10 µM (see FIG. 14). Slightly higher concentrations have previously reported for chlorpromazine ($IC_{50}$=10-100 µM), indicating that the assay method used may affect the magnitude of the obtained $IC_{50}$ value. This discrepancy could be due to the relative timescales involved. Since many traditional assays (e.g. radiometric assays) are very time consuming and do not allow for continuous monitoring of enzymatic activity, quantitation may occur after the lag phase has completed and the burst phase has begun. Accordingly, a relatively small amount of remaining active enzyme could result in a large response and, therefore, a larger concentration of inhibitor might be needed to obtain the same apparent inhibition as in a faster assay. If this discrepancy proves consistent with other inhibitor systems, the advantage of natural substrate presentation in addition to the real time measurements offered by this assay may prove critical in the future development of drug candidates. Moreover, unlike with electroactive or fluorometric systems, the present system is less likely to be perturbed by charged or highly conjugated inhibitors

REFERENCES

1. Kugiyama, K.; Ota, Y.; Takazoe, K.; Moriyama, Y.; Kawano, H.; Miyao, Y.; Sakamoto, T.; Soejima, H.; Ogawa, H.; Doi, H.; Sugiyama, S.; Yasue, H., Circulating levels of secretory type II phospholipase A(2) predict coronary events in patients with coronary artery disease. Circulation 1999, 100, (12), 1280-1284.
2. Agarwal, N.; Pitchumoni, C. S., Assessment of severity in acute-pancreatitis. American Journal of Gastroenterology 1991, 86, (10), 1385-1391.
3. Green, J. A.; Smith, G. M.; Buchta, R.; Lee, R.; Ho, K. Y.; Rajkovic, I. A.; Scott, K. F., Circulating Phospholipase-A2 Activity Associated With Sepsis And Septic Shock Is Indistinguishable From That Associated With Rheumatoid-Arthritis. Inflammation 1991, 15, (5), 355-367.
4. Abe, T.; Sakamoto, K.; Kamohara, H.; Hirano, Y.; Kuwahara, N.; Ogawa, M., Group II phospholipase A2 is increased in peritoneal and pleural effusions in patients with various types of cancer. International Journal of Cancer 1997, 74, (3), 245-250.
5. Sarda, L.; Desnuelle, P., Action de la lipase pancréatique sur les esters en émulsion. Biochimica Et Biophysica Acta 1958, 30, (3).
6. Burack, W. R.; Dibble, A. R. G.; Allietta, M. M.; Biltonen, R. L., Changes in vesicle morphology induced by lateral phase separation modulate phospholipase A(2) activity. Biochemistry 1997, 36, (34), 10551-10557.
7. Lehtonen, J. Y. A.; Kinnunen, P. K. J., Phospholipase A2 as a mechanosensor. Biophysical Journal 1995, 68, 1888-1894.
8. Rose, T. M.; Prestwich, G. D., Fluorogenic phospholipids as head group-selective reporters of phospholipase A activity. Acs Chemical Biology 2006, 1, (2), 83-92.
9. Chemburu, S.; Ji, E.; Casana, Y.; Wu, Y.; Buranda, T.; Schanze, K. S.; Lopez, G. P.; Whitten, D. G., Conjugated Polyelectrolyte Supported Bead Based Assays for Phospholipase A(2) Activity. Journal of Physical Chemistry B 2008, 112, (46), 14492-14499.
10. Okada, S. Y.; Jelinek, R.; Charych, D., Induced color change of conjugated polymeric vesicles by interfacial catalysis of phospholipase A(2). Angewandte Chemie-International Edition 1999, 38, (5), 655-659.
11. Rex, S.; Schwarz, G., Quantitative studies on the melittin-induced leakage mechanism of lipid vesicles. Biochemistry 1998, 37, (8), 2336-2345.
12. Fugman, D. A.; Shirai, K.; Jackson, R. L.; Johnson, J. D., Lipoprotein Lipase-A2-Catalyzed And Phospholipase-A2-Catalyzed Hydrolysis Of Phospholipid-Vesicles With An Encapsulated Fluorescent Dye—Effects Of Apolipoproteins. Biochimica Et Biophysica Acta 1984, 795, (2), 191-195.
13. Lelkes, P. I.; Tandeter, H. B., Studies on the methodology of the carboxyfluorescein assay and on the mechanism of liposome stabilization by red-blood-cells invitro. Biochimica Et Biophysica Acta 1982, 716, (3), 410-419.
14. Kim, H. J.; Bennetto, H. P.; Halablab, M. A.; Choi, C. H.; Yoon, S., Performance of an electrochemical sensor with different types of liposomal mediators for the detection of hemolytic bacteria. Sensors and Actuators B-Chemical 2006, 119, (1), 143-149.
15. Zeineldin, R.; Piyasena, M. E.; Sklar, L. A.; Whitten, D.; Lopez, G. P., Detection of membrane biointeractions based on fluorescence superquenching. Langmuir 2008, 24, (8), 4125-4131.
16. Aili, D.; Tai, F.-T.; Enander, K.; Baltzer, L.; Liedberg, B., Self-Assembly of Fibers and Nanorings from Disulfide-Linked Helix-Loop-Helix Polypeptides. Angewandte Chemie International Edition 2008, 47, 5554-5556.
17. Wilschut, J. C.; Regts, J.; Scherphof, G., Action of phospholipase A2 on phospholipid vesicles: perseration of the membrane permeability barrier during asymmetric bilayer degradation. FEBS Letters 1979, 98, (1), 181-186.
18. Lindahl, M.; Tagesson, C., Selective inhibition of group II phospholipase A2 by quercetin. Inflammation 1993, 17, (5), 573-582.
19. Gelb, M. H.; Jain, M. K.; Berg, O., Inhibition of phospholipase A(2). FASEB J 1994, 8, (12), 916-924.

20. Olson, F.; Hunt, C. A.; Szoka, F. C.; Vail, W. J.; Papahadjopoulos, D., Preparation of liposomes of defined size distribution by extrusion through polycarbonate membranes. *Biochimica Et Biophysica Acta* 1979, 557, (1), 9-23.
21. Stewart, J. C. M., Colorometric determination of phospholipids with ammonium ferrothiocyanate. *Analytical Biochemistry,* 1980, 104, (1), 10-14.
22. Dimitrovaa, M. N.; Matsumura, H.; Dimitrovab, A.; Neitchevb, V. Z., Interaction of albumins from different species with phospholipid liposomes. Multiple binding sites system *International Journal of Biological Macromolecules,* 2000, 27, (1), 187-194.
23. C. S. Peyratout, L. Dáhne, Tailor-made polyelectrolyte microcapsules: From multilayers to smart containers. *Angewandte Chemie International Edition,* 2004, 43, 3762-3783;
24. W. Meier. Polymer nanocapsules. *Chemical Society Reviews,* 2000, 29, 295-303.
25. Zhao et al. Paper-based bioassays using gold nanoparticle colorimetric probes. *Analytical Chemistry,* 2008, 80(22) pp 8431-8437.
26. Aili, D., Enander, K., Baltzer, L., Liedberg, B. Assembly of polypeptide-functionalized gold nanoparticles through a heteroassociation and folding-dependent bridging *Nano Letters,* 2008, 8, 2473-2478.
27. MacKay et al. HIV TAT Peptide Modifies the Distribution of DNA Nanolipoparticles Following Convection-enhanced Delivery, *Molecular Therapy* 2008, 16, 5, 893-900

The invention claimed is:
1. A composition comprising:
    a) a plurality of signal particles functionalised with at least one binding moiety;
    b) a plurality of carrier particles;
    c) a plurality of linker molecules contained within said carrier particles, wherein said linker molecules are capable of associating with the at least one binding moiety on said signal particles to cause aggregation of said signal particles.
2. The composition of claim 1, wherein said signal particles comprise particles that produce a measurable change upon aggregation.
3. The composition of claim 2, wherein said measurable change comprises a change in optical absorption.
4. The composition of claim 1, wherein said signal particles are selected from the group consisting of microparticles and nanoparticles.
5. The composition of claim 4, wherein said nanoparticles are selected from the group consisting of spherical nanoparticles, nanotubes, nanorods, metal nanoparticles, semiconducting nanoparticles, core-shell nanoparticles, polymer nanoparticles, gold nanoparticles, silver nanoparticles, nanoparticles comprising ferrous or cobalt-based metals, quantum dots, polymer microcapsules and polymer nanocapsules.
6. The composition of claim 1, wherein said at least one binding moiety comprises a carbohydrate or a polymer.
7. The composition of claim 6 wherein said polymer is a polypeptide.

SEQUENCE LISTING

```
<160> NUMBER OF SEQ ID NOS: 2

<210> SEQ ID NO 1
<211> LENGTH: 42
<212> TYPE: PRT
<213> ORGANISM: Artificial sequence
<220> FEATURE:
<223> OTHER INFORMATION: JR2EC polypeptide

<400> SEQUENCE: 1

Asn Ala Ala Asp Leu Glu Lys Ala Ile Glu Ala Leu Glu Lys His Leu
1               5                   10                  15

Glu Ala Lys Gly Pro Cys Asp Ala Ala Gln Leu Glu Lys Gln Leu Glu
            20                  25                  30

Gln Ala Phe Glu Ala Phe Glu Arg Ala Gly
        35                  40

<210> SEQ ID NO 2
<211> LENGTH: 42
<212> TYPE: PRT
<213> ORGANISM: Artificial sequence
<220> FEATURE:
<223> OTHER INFORMATION: JR2KC polypeptide

<400> SEQUENCE: 2

Asn Ala Ala Asp Leu Lys Lys Ala Ile Lys Ala Leu Lys Lys His Leu
1               5                   10                  15

Lys Ala Lys Gly Pro Cys Asp Ala Ala Gln Leu Lys Lys Gln Leu Lys
            20                  25                  30

Gln Ala Phe Lys Ala Phe Lys Arg Ala Gly
        35                  40
```

8. The composition of claim 1, wherein said carrier particle comprises a liquid core surrounded by a surface layer.

9. The composition of claim 8 wherein the surface layer of said carrier particle is specifically degradable by an enzyme or an antimicrobial peptide.

10. The composition of claim 8, wherein said surface layer comprises amphipathic molecules.

11. The composition of claim 10, wherein said amphipathic molecules are selected from the group comprising lipids and artificially generated amphipathic molecules.

12. The composition of claim 1, wherein said carrier particle is selected from the group consisting of liposomes, micelles, nanocapsules, microcapsules and polymeric particles.

13. The composition of claim 1, wherein each linker molecule is:
(a) capable of associating with at least one binding moiety on a first signal particle, and at least one binding moiety on a second signal particle; or
b) capable of associating with two or more binding moieties on each signal particle; or
c) a polymer.

14. The composition of claim 1, wherein said composition additionally comprises:
(a) a compound which modifies the rate or extent of enzymatic activity; and/or
(b) a preservative.

15. An assay device for detection of an analyte in a sample, wherein said assay device comprises the composition of claim 1, and wherein said analyte is capable of degrading said carrier particle to release said linker molecule from said carrier particle, wherein said analyte is optionally an enzyme.

16. The assay device of claim 15, wherein said analyte is an enzyme.

17. The assay device of claim 16, wherein said enzyme is a lipase.

18. The assay device of claim 17, wherein said lipase is a phospholipase.

19. A kit for detection of an analyte in a sample, said kit comprising the composition of claim 1.

20. A method for detecting an analyte in a sample comprising the steps of:
i) contacting said sample with the composition according to claim 1, wherein said analyte degrades said carrier particles, releasing said linker molecules from said carrier particles; and
ii) detecting aggregation of said signal particles.

21. The method of claim 20, wherein said analyte is an enzyme.

22. The method of claim 21, wherein said enzyme is a lipase.

23. The method of claim 22, wherein said lipase is a phospholipase.

24. A method of diagnosing a disease or condition associated with dysregulation of an enzyme in a subject comprising the steps of:

i) contacting a sample from said subject with the composition according to claim 1, wherein said enzyme degrades said carrier particles, releasing said linker molecules from said carrier particles;
ii) detecting aggregation of said signal particles;
iii) comparing the extent of aggregation of said signal particles in the sample with the extent of aggregation produced by normal enzyme concentration or enzymatic activity; and
iv) determining a deviation from the normal enzyme concentration or enzymatic activity;
thereby diagnosing a disease or condition associated with dysregulation of an enzyme in a subject.

25. The method of claim 24 wherein:
a) step i) further comprises the addition of a compound which modifies the rate or extent of enzymatic activity; and/or
b) step ii) comprises detecting a measurable change in optical absorption, optical scattering, fluorescence, luminescence, optical extinction, magnetic properties, electrochemical potential, viscosity, diffusion kinetics or optical polarisation.

26. A method for screening for a modulator of enzymatic activity comprising the steps of:
i) contacting said enzyme with a test substance or test mixture and the composition according to claim 1;
ii) detecting aggregation of said signal particles;
iii) comparing the extent of aggregation of said signal particles in the sample with the extent of aggregation produced in the absence of the test substance or test mixture; and
iv) determining whether the test substance or test mixture has increased or decreased enzymatic activity;
thereby screening for a modulator of enzymatic activity.

27. The method of claim 26 wherein:
(a) step i) further comprises the addition of a compound which modifies the rate or extent of enzymatic activity; and/or
(b) step ii) comprises detecting a measurable change in optical absorption, optical scattering, fluorescence, luminescence, optical extinction, magnetic properties, electrochemical potential, viscosity, diffusion kinetics or optical polarisation.

28. A method of screening for candidate antimicrobial peptides comprising the steps of:
i) contacting a test substance or test mixture with the composition according to claim 1; and
ii) detecting aggregation of said signal particles;
wherein any significant aggregation of said signal particles indicates that the test substance or test mixture is or contains a candidate antimicrobial peptide.

29. A method for detecting toxins comprising the steps of:
i) contacting a test substance or test mixture with the composition of claim 1; and
ii) detecting aggregation of said signal particles;
wherein any significant aggregation of said signal particles indicates that the test substance or test mixture is or contains a toxin.

* * * * *